US008632453B2

(12) United States Patent
Chu et al.

(10) Patent No.: US 8,632,453 B2
(45) Date of Patent: *Jan. 21, 2014

(54) SPACER FOR SLING DELIVERY SYSTEM

(75) Inventors: Michael S. H. Chu, Brookline, MA (US); Alfred P. Intoccia, Jr., Amherst, NH (US); Michael G. McGrath, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1585 days.

This patent is subject to a terminal disclaimer.

(21) Appl. No.: 12/218,533

(22) Filed: Jul. 15, 2008

(65) Prior Publication Data

US 2009/0069628 A1 Mar. 12, 2009

Related U.S. Application Data

(63) Continuation of application No. 10/641,376, filed on Aug. 14, 2003, now Pat. No. 7,402,133.

(60) Provisional application No. 60/434,167, filed on Dec. 17, 2002, provisional application No. 60/449,465, filed on Feb. 24, 2003.

(51) Int. Cl.
*A61F 2/00* (2006.01)

(52) U.S. Cl.
USPC ............................................. 600/37

(58) Field of Classification Search
USPC .......... 600/29–31, 37; 128/DIG. 25, 897, 898
See application file for complete search history.

(56) References Cited

U.S. PATENT DOCUMENTS

| 246,648 A | 9/1881 | Wilcox |
| 1,179,910 A | 4/1916 | Greenfield |
| 1,310,982 A | 7/1919 | Davis |
| 1,417,669 A | 5/1922 | Langworthy |
| 1,517,787 A | 12/1924 | Langbein |
| 1,612,697 A | 12/1926 | Cedl |
| 1,677,671 A | 7/1928 | Councill |
| 2,113,246 A | 4/1938 | Wappler |
| 2,199,025 A | 4/1940 | Conn |
| 2,200,120 A | 5/1940 | Nauth |
| 2,454,680 A | 11/1948 | Stephens |
| 2,487,502 A | 11/1949 | Willinsky |
| 2,556,783 A | 6/1951 | Wallace |
| 2,635,238 A | 4/1953 | Garland |

(Continued)

FOREIGN PATENT DOCUMENTS

| CA | 2198778 | 3/1996 |
| DE | 2 305 815 | 8/1974 |

(Continued)

OTHER PUBLICATIONS

Bayer et al., "A New Approach to Primary Strengthening of Colostomy with Marlex® Mesh to Prevent Paracolostomy Hernia," Surgery, Gynecology & Obstetrics, Dec. 1986, vol. 163, pp. 579-580.

(Continued)

*Primary Examiner* — Samuel Gilbert

(57) ABSTRACT

The invention features systems, methods, and devices relating to delivering a sling to an anatomical site in the body of a patient.

25 Claims, 23 Drawing Sheets

(56) References Cited

U.S. PATENT DOCUMENTS

| | | |
|---|---|---|
| 2,655,921 A | 10/1953 | Haboush |
| 2,666,430 A | 1/1954 | Gispert |
| 2,671,444 A | 3/1954 | Pease, Jr. |
| 2,738,790 A | 3/1956 | Todt, Sr. et al. |
| 2,751,903 A | 6/1956 | Ivory et al. |
| 2,917,878 A | 12/1959 | Edwin et al. |
| 3,003,155 A | 10/1961 | Mielzynski et al. |
| 3,054,406 A | 9/1962 | Usher |
| 3,124,136 A | 3/1964 | Usher |
| 3,181,533 A | 5/1965 | Heath |
| 3,212,502 A | 10/1965 | Myers |
| 3,314,431 A | 4/1967 | Smith, Jr. |
| 3,364,200 A | 1/1968 | Ashton et al. |
| 3,388,847 A | 6/1968 | Kasulin et al. |
| 3,551,987 A | 1/1971 | Wilkinson |
| 3,580,313 A | 5/1971 | McKnight |
| 3,593,903 A | 7/1971 | Astafiev et al. |
| 3,596,656 A | 8/1971 | Kaute |
| 3,620,212 A | 11/1971 | Fannon, Jr. et al. |
| 3,666,750 A | 5/1972 | Briskin et al. |
| 3,699,969 A | 10/1972 | Allen |
| 3,705,575 A | 12/1972 | Edwards |
| 3,710,592 A | 1/1973 | Scow |
| 3,710,795 A | 1/1973 | Higuchi et al. |
| 3,739,784 A | 6/1973 | Itoh |
| 3,744,495 A | 7/1973 | Johnson |
| 3,823,705 A | 7/1974 | Trimble |
| 3,857,396 A | 12/1974 | Hardwick |
| 3,875,937 A | 4/1975 | Schmitt et al. |
| 3,877,434 A | 4/1975 | Ferguson et al. |
| 3,890,977 A | 6/1975 | Wilson |
| 3,892,232 A | 7/1975 | Neufeld |
| 3,918,455 A | 11/1975 | Coplan |
| 3,937,223 A | 2/1976 | Roth |
| 3,995,619 A | 12/1976 | Glatzer |
| 4,006,747 A | 2/1977 | Kronenthal et al. |
| 4,065,816 A | 1/1978 | Sawyer |
| 4,085,756 A | 4/1978 | Weaver |
| 4,159,716 A | 7/1979 | Borchers |
| 4,172,458 A | 10/1979 | Pereyra |
| 4,175,557 A | 11/1979 | Hung |
| 4,193,137 A | 3/1980 | Heck |
| 4,217,890 A | 8/1980 | Owens |
| 4,347,847 A | 9/1982 | Usher |
| 4,363,319 A | 12/1982 | Altshuler |
| 4,367,816 A | 1/1983 | Wilkes |
| 4,371,124 A | 2/1983 | Gifford et al. |
| 4,391,869 A | 7/1983 | Cook et al. |
| 4,392,495 A | 7/1983 | Bayers |
| 4,400,833 A | 8/1983 | Kurland |
| 4,409,974 A | 10/1983 | Freedland |
| 4,414,967 A | 11/1983 | Shapiro |
| 4,415,111 A | 11/1983 | McHarrie et al. |
| 4,421,112 A | 12/1983 | Mains et al. |
| 4,422,567 A | 12/1983 | Haynes |
| 4,438,769 A | 3/1984 | Pratt et al. |
| 4,445,898 A | 5/1984 | Jensen |
| 4,452,245 A | 6/1984 | Usher |
| 4,520,821 A | 6/1985 | Schmidt et al. |
| 4,527,726 A | 7/1985 | Assell et al. |
| 4,535,768 A | 8/1985 | Hourahane et al. |
| 4,537,185 A | 8/1985 | Stednitz |
| 4,545,374 A | 10/1985 | Jacobson |
| 4,549,545 A | 10/1985 | Levy |
| 4,569,469 A | 2/1986 | Mongeon et al. |
| 4,576,167 A | 3/1986 | Noiles |
| 4,592,339 A | 6/1986 | Kuzmak et al. |
| 4,606,335 A | 8/1986 | Wedeen |
| 4,606,343 A | 8/1986 | Conta et al. |
| 4,614,187 A | 9/1986 | Mulhollan et al. |
| 4,625,726 A | 12/1986 | Duthoy |
| 4,632,100 A | 12/1986 | Somers et al. |
| 4,633,871 A | 1/1987 | Shinozuka |
| 4,633,873 A | 1/1987 | Dumican et al. |
| 4,635,634 A | 1/1987 | Santos |
| 4,652,264 A | 3/1987 | Dumican |
| 4,655,219 A | 4/1987 | Petruzzi |
| 4,655,221 A | 4/1987 | Devereux |
| 4,664,305 A | 5/1987 | Blake, III et al. |
| 4,665,906 A | 5/1987 | Jervis |
| 4,669,473 A | 6/1987 | Richards et al. |
| 4,688,555 A | 8/1987 | Wardle |
| 4,691,705 A | 9/1987 | Okada |
| 4,694,781 A | 9/1987 | Howe et al. |
| 4,705,040 A | 11/1987 | Mueller et al. |
| 4,738,255 A | 4/1988 | Goble et al. |
| 4,739,751 A | 4/1988 | Sapega et al. |
| 4,741,330 A | 5/1988 | Hayhurst |
| 4,741,335 A | 5/1988 | Okada |
| 4,744,353 A | 5/1988 | McFarland |
| 4,750,492 A | 6/1988 | Jacobs |
| 4,763,669 A | 8/1988 | Jaeger |
| 4,768,505 A | 9/1988 | Okada et al. |
| 4,769,038 A | 9/1988 | Bendavid et al. |
| 4,776,337 A | 10/1988 | Palmaz |
| 4,784,126 A | 11/1988 | Hourahane |
| 4,784,137 A | 11/1988 | Kulik et al. |
| 4,784,138 A | 11/1988 | Sinnett |
| 4,838,884 A | 6/1989 | Dumican et al. |
| 4,854,316 A | 8/1989 | Davis |
| 4,857,041 A | 8/1989 | Annis et al. |
| 4,870,957 A | 10/1989 | Goble et al. |
| 4,872,451 A | 10/1989 | Moore et al. |
| 4,873,977 A | 10/1989 | Avant et al. |
| 4,880,015 A | 11/1989 | Nierman |
| 4,883,048 A | 11/1989 | Purnell et al. |
| 4,889,119 A | 12/1989 | Jamiolkowski et al. |
| 4,898,156 A | 2/1990 | Gatturna et al. |
| 4,899,743 A | 2/1990 | Nicholson et al. |
| 4,905,692 A | 3/1990 | More |
| 4,909,789 A | 3/1990 | Taguchi et al. |
| 4,911,165 A | 3/1990 | Lennard et al. |
| 4,920,958 A | 5/1990 | Walt et al. |
| 4,920,986 A | 5/1990 | Biswas |
| 4,926,722 A | 5/1990 | Sorensen et al. |
| 4,938,760 A | 7/1990 | Burton et al. |
| 4,940,467 A | 7/1990 | Tronzo |
| 4,944,741 A | 7/1990 | Hasson |
| 4,945,920 A | 8/1990 | Qossick |
| 4,946,468 A | 8/1990 | Li |
| 4,957,498 A | 9/1990 | Caspari et al. |
| 4,960,420 A | 10/1990 | Goble et al. |
| 4,968,315 A | 11/1990 | Gatturna |
| 4,969,892 A | 11/1990 | Burton et al. |
| 4,973,300 A | 11/1990 | Wright |
| 4,978,351 A | 12/1990 | Rozas |
| 4,986,831 A | 1/1991 | King et al. |
| 4,988,339 A | 1/1991 | Vadher |
| 4,997,433 A | 3/1991 | Goble et al. |
| 4,997,434 A | 3/1991 | Seedhom et al. |
| 4,997,436 A | 3/1991 | Oberlander |
| 5,002,550 A | 3/1991 | Li |
| 5,002,551 A | 3/1991 | Linsky et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,026,398 A | 6/1991 | May et al. |
| 5,030,219 A | 7/1991 | Matsen, III et al. |
| 5,036,867 A | 8/1991 | Biswas |
| 5,040,715 A | 8/1991 | Green et al. |
| 5,046,513 A | 9/1991 | Gatturna et al. |
| 5,052,607 A | 10/1991 | Dutton |
| 5,057,112 A | 10/1991 | Sherman et al. |
| 5,057,114 A | 10/1991 | Wittich et al. |
| 5,059,199 A | 10/1991 | Okada et al. |
| 5,061,181 A | 10/1991 | Niznick |
| 5,064,434 A | 11/1991 | Haber |
| 5,078,730 A | 1/1992 | Li et al. |
| 5,078,731 A | 1/1992 | Hayhurst |
| 5,080,674 A | 1/1992 | Jacobs et al. |
| 5,084,058 A | 1/1992 | Li |
| 5,085,661 A | 2/1992 | Moss |

(56) References Cited

U.S. PATENT DOCUMENTS

| | | |
|---|---|---|
| 5,087,263 A | 2/1992 | Li |
| 5,088,323 A | 2/1992 | Johnson et al. |
| 5,089,013 A | 2/1992 | Bezwada et al. |
| 5,098,440 A | 3/1992 | Hillstead |
| 5,100,417 A | 3/1992 | Cerier et al. |
| 5,102,421 A | 4/1992 | Anspach, Jr. |
| 5,108,397 A | 4/1992 | White |
| 5,112,337 A | 5/1992 | Paulos et al. |
| 5,112,344 A | 5/1992 | Petros |
| 5,116,338 A | 5/1992 | Poggie et al. |
| 5,122,155 A | 6/1992 | Eberbach |
| 5,123,924 A | 6/1992 | Sioshansi et al. |
| 5,129,902 A | 7/1992 | Goble et al. |
| 5,133,723 A | 7/1992 | Li et al. |
| 5,141,520 A | 8/1992 | Goble et al. |
| 5,147,374 A | 9/1992 | Fernandez |
| 5,149,329 A | 9/1992 | Richardson |
| 5,152,279 A | 10/1992 | Wilk |
| 5,152,749 A | 10/1992 | Giesy et al. |
| 5,152,790 A | 10/1992 | Rosenberg et al. |
| 5,156,315 A | 10/1992 | Green et al. |
| 5,163,942 A | 11/1992 | Rydell |
| 5,163,946 A | 11/1992 | Li |
| 5,174,300 A | 12/1992 | Bales et al. |
| 5,176,692 A | 1/1993 | Wilk et al. |
| 5,178,630 A | 1/1993 | Schmitt |
| 5,180,388 A | 1/1993 | DiCarlo |
| 5,188,636 A | 2/1993 | Fedotov |
| 5,192,008 A | 3/1993 | Hwan |
| 5,192,303 A | 3/1993 | Gatturna et al. |
| 5,195,542 A | 3/1993 | Gazielly et al. |
| 5,197,968 A | 3/1993 | Clement |
| 5,203,784 A | 4/1993 | Ross et al. |
| 5,203,787 A | 4/1993 | Noblitt et al. |
| 5,207,679 A | 5/1993 | Li |
| 5,209,747 A | 5/1993 | Knoepfler |
| 5,217,462 A | 6/1993 | Asnis et al. |
| 5,217,486 A | 6/1993 | Rice et al. |
| 5,222,508 A | 6/1993 | Contarini |
| 5,224,946 A | 7/1993 | Hayhurst et al. |
| 5,236,445 A | 8/1993 | Hayhurst et al. |
| 5,242,457 A | 9/1993 | Akopov et al. |
| 5,250,033 A | 10/1993 | Evans et al. |
| 5,251,638 A | 10/1993 | Cottone, Jr. et al. |
| 5,254,130 A | 10/1993 | Poncet et al. |
| 5,254,133 A | 10/1993 | Seid |
| 5,256,133 A | 10/1993 | Spitz |
| 5,256,150 A | 10/1993 | Quiachon et al. |
| 5,258,000 A | 11/1993 | Gianturco |
| 5,258,016 A | 11/1993 | DiPoto et al. |
| 5,263,969 A | 11/1993 | Phillips |
| 5,268,001 A | 12/1993 | Nicholson et al. |
| 5,279,311 A | 1/1994 | Snyder |
| 5,281,237 A | 1/1994 | Gimpelson |
| 5,282,812 A | 2/1994 | Suarez, Jr. |
| 5,289,963 A | 3/1994 | McGarry et al. |
| 5,290,217 A | 3/1994 | Campos |
| 5,290,294 A | 3/1994 | Cox et al. |
| 5,292,328 A | 3/1994 | Hain et al. |
| 5,304,220 A | 4/1994 | Maginot |
| 5,311,858 A | 5/1994 | Adair |
| 5,312,433 A | 5/1994 | Boebel et al. |
| 5,316,543 A | 5/1994 | Eberbach |
| 5,328,077 A | 7/1994 | Lou |
| 5,333,624 A | 8/1994 | Tovey |
| 5,334,208 A | 8/1994 | Soehendra et al. |
| 5,337,736 A | 8/1994 | Reddy |
| 5,354,292 A | 10/1994 | Braeuer et al. |
| 5,356,064 A | 10/1994 | Green et al. |
| 5,362,294 A | 11/1994 | Seitzinger |
| 5,364,002 A | 11/1994 | Green et al. |
| 5,364,406 A | 11/1994 | Sewell, Jr. |
| 5,366,460 A | 11/1994 | Eberbach |
| 5,366,479 A | 11/1994 | McGarry et al. |
| 5,368,595 A | 11/1994 | Lewis et al. |
| 5,368,602 A | 11/1994 | de la Torre |
| 5,370,282 A | 12/1994 | Sedlmeier |
| 5,370,650 A | 12/1994 | Tovey et al. |
| 5,370,662 A | 12/1994 | Stone et al. |
| 5,372,146 A | 12/1994 | Branch |
| 5,376,094 A | 12/1994 | Kline |
| 5,379,933 A | 1/1995 | Green et al. |
| 5,381,943 A | 1/1995 | Allen et al. |
| 5,383,477 A | 1/1995 | DeMatteis |
| 5,383,928 A | 1/1995 | Scott et al. |
| 5,397,332 A | 3/1995 | Kammerer et al. |
| 5,411,506 A | 5/1995 | Goble et al. |
| 5,417,203 A | 5/1995 | Tovey et al. |
| 5,417,712 A | 5/1995 | Whittaker et al. |
| 5,423,860 A | 6/1995 | Lizardi et al. |
| 5,425,489 A | 6/1995 | Shichman et al. |
| 5,425,737 A | 6/1995 | Burbank et al. |
| 5,425,743 A | 6/1995 | Nicholas |
| 5,425,984 A | 6/1995 | Kennedy et al. |
| 5,431,173 A | 7/1995 | Chin et al. |
| 5,437,603 A | 8/1995 | Cerny et al. |
| 5,441,502 A | 8/1995 | Bartlett |
| 5,441,508 A | 8/1995 | Gazielly et al. |
| 5,443,482 A | 8/1995 | Stone et al. |
| 5,451,235 A | 9/1995 | Lock et al. |
| 5,456,722 A | 10/1995 | McCleod et al. |
| 5,474,543 A | 12/1995 | McKay |
| 5,499,991 A | 3/1996 | Garman et al. |
| 5,500,001 A | 3/1996 | Trott |
| 5,501,683 A | 3/1996 | Trott |
| 5,501,690 A | 3/1996 | Measamer et al. |
| 5,507,754 A | 4/1996 | Green et al. |
| 5,507,796 A | 4/1996 | Hasson |
| 5,520,696 A | 5/1996 | Wenstrom, Jr. |
| 5,520,700 A | 5/1996 | Beyar et al. |
| 5,522,843 A | 6/1996 | Zang |
| 5,522,845 A | 6/1996 | Wenstrom, Jr. |
| 5,527,341 A | 6/1996 | Gogolewski et al. |
| 5,538,427 A | 7/1996 | Hoffman et al. |
| 5,540,703 A | 7/1996 | Barker et al. |
| 5,544,644 A | 8/1996 | Benderev et al. |
| 5,549,617 A | 8/1996 | Green et al. |
| 5,549,619 A | 8/1996 | Peters et al. |
| 5,562,689 A | 10/1996 | Green et al. |
| 5,569,273 A | 10/1996 | Titone et al. |
| 5,571,117 A | 11/1996 | Ahn |
| 5,573,548 A | 11/1996 | Nazre et al. |
| 5,578,057 A | 11/1996 | Wenstrom, Jr. |
| 5,582,188 A | 12/1996 | Benderev et al. |
| 5,584,695 A | 12/1996 | Lal Sachdeva et al. |
| 5,584,835 A | 12/1996 | Greenfield |
| 5,591,163 A | 1/1997 | Thompson |
| 5,591,207 A | 1/1997 | Coleman |
| 5,601,575 A | 2/1997 | Measamer et al. |
| 5,607,432 A | 3/1997 | Fucci |
| 5,611,515 A | 3/1997 | Benderev et al. |
| 5,618,413 A | 4/1997 | Todd et al. |
| 5,620,012 A | 4/1997 | Benderev et al. |
| 5,624,446 A | 4/1997 | Harryman, II |
| 5,634,931 A | 6/1997 | Kugel |
| 5,634,944 A | 6/1997 | Magram |
| 5,637,112 A | 6/1997 | Moore et al. |
| 5,639,274 A | 6/1997 | Fischell et al. |
| 5,641,502 A | 6/1997 | Skalla et al. |
| 5,641,566 A | 6/1997 | Kranzler et al. |
| 5,643,288 A | 7/1997 | Thompson |
| 5,643,320 A | 7/1997 | Lower et al. |
| 5,643,596 A | 7/1997 | Pruss et al. |
| 5,645,589 A | 7/1997 | Li |
| 5,645,849 A | 7/1997 | Pruss et al. |
| 5,645,915 A | 7/1997 | Kranzler et al. |
| 5,647,836 A | 7/1997 | Blake, III et al. |
| 5,649,940 A | 7/1997 | Hart et al. |
| 5,653,373 A | 8/1997 | Green et al. |
| 5,658,296 A | 8/1997 | Bates et al. |
| 5,660,854 A | 8/1997 | Haynes et al. |
| 5,662,654 A | 9/1997 | Thompson |
| 5,662,658 A | 9/1997 | Wenstrom, Jr. |
| 5,674,247 A | 10/1997 | Sohn |

(56) References Cited

U.S. PATENT DOCUMENTS

| | | |
|---|---|---|
| 5,681,301 A | 10/1997 | Yang et al. |
| 5,681,310 A | 10/1997 | Yuan et al. |
| 5,681,352 A | 10/1997 | Clancy, III et al. |
| 5,683,378 A | 11/1997 | Christy |
| 5,683,418 A | 11/1997 | Luscombe et al. |
| 5,690,649 A | 11/1997 | Li |
| 5,690,655 A | 11/1997 | Hart et al. |
| 5,690,677 A | 11/1997 | Schmieding et al. |
| 5,697,931 A | 12/1997 | Thompson |
| 5,700,266 A | 12/1997 | Harryman, II |
| 5,700,286 A | 12/1997 | Tartaglia et al. |
| 5,702,215 A | 12/1997 | Li |
| 5,702,397 A | 12/1997 | Goble et al. |
| 5,702,415 A | 12/1997 | Matthai et al. |
| 5,707,647 A | 1/1998 | Dunn et al. |
| 5,725,529 A | 3/1998 | Nicholson et al. |
| 5,725,557 A | 3/1998 | Gattuma et al. |
| 5,728,100 A | 3/1998 | Skiba |
| 5,733,337 A | 3/1998 | Carr, Jr. et al. |
| 5,742,943 A | 4/1998 | Chen |
| 5,752,963 A | 5/1998 | Allard et al. |
| 5,766,221 A | 6/1998 | Benderev et al. |
| 5,769,864 A | 6/1998 | Kugel |
| 5,776,184 A | 7/1998 | Tuch |
| 5,782,834 A | 7/1998 | Lucey et al. |
| 5,782,862 A | 7/1998 | Bonutti |
| 5,785,640 A | 7/1998 | Kresch et al. |
| 5,788,710 A | 8/1998 | Bates et al. |
| 5,807,403 A | 9/1998 | Beyar et al. |
| 5,813,975 A | 9/1998 | Valenti |
| 5,814,051 A | 9/1998 | Wenstrom, Jr. |
| 5,814,071 A | 9/1998 | McDevitt et al. |
| 5,814,072 A | 9/1998 | Bonutti |
| 5,816,258 A | 10/1998 | Jervis |
| 5,824,029 A | 10/1998 | Weijand et al. |
| 5,824,049 A | 10/1998 | Ragheb et al. |
| 5,824,082 A | 10/1998 | Brown |
| 5,827,291 A | 10/1998 | Fucci et al. |
| 5,836,314 A | 11/1998 | Benderev et al. |
| 5,836,315 A | 11/1998 | Benderev et al. |
| 5,836,961 A | 11/1998 | Kieturakis et al. |
| 5,840,011 A | 11/1998 | Landgrebe et al. |
| 5,842,478 A | 12/1998 | Benderev et al. |
| 5,849,004 A | 12/1998 | Bramlet |
| 5,851,210 A | 12/1998 | Torossian |
| 5,851,219 A | 12/1998 | Goble et al. |
| 5,860,993 A | 1/1999 | Thompson et al. |
| 5,868,747 A | 2/1999 | Ochoa et al. |
| 5,868,789 A | 2/1999 | Huebner |
| 5,871,503 A | 2/1999 | Bartlett |
| 5,899,909 A | 5/1999 | Claren et al. |
| 5,916,225 A | 6/1999 | Kugel |
| 5,922,026 A | 7/1999 | Chin |
| 5,934,283 A | 8/1999 | Willem et al. |
| 5,935,122 A | 8/1999 | Fourkas et al. |
| 5,935,138 A | 8/1999 | McJames, II et al. |
| 5,954,057 A | 9/1999 | Li |
| 5,957,932 A | 9/1999 | Bates et al. |
| 5,972,000 A | 10/1999 | Beyar et al. |
| 5,989,180 A | 11/1999 | Norton |
| 5,997,554 A | 12/1999 | Thompson |
| 6,010,447 A | 1/2000 | Kardjian |
| 6,030,337 A | 2/2000 | Grant et al. |
| 6,030,393 A | 2/2000 | Corlew |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,050,937 A | 4/2000 | Benderev |
| 6,056,687 A | 5/2000 | Polyak et al. |
| 6,059,801 A | 5/2000 | Samimi |
| 6,068,591 A | 5/2000 | Bruckner et al. |
| 6,077,216 A | 6/2000 | Benderev et al. |
| 6,090,116 A | 7/2000 | D'Aversa et al. |
| 6,099,538 A | 8/2000 | Moses et al. |
| 6,099,547 A | 8/2000 | Gellman et al. |
| 6,102,921 A | 8/2000 | Zhu et al. |
| 6,110,101 A | 8/2000 | Tihon et al. |
| 6,113,611 A | 9/2000 | Allen et al. |
| 6,117,067 A | 9/2000 | Gil-Vernet |
| 6,168,801 B1 | 1/2001 | Heil, Jr. et al. |
| 6,200,261 B1 | 3/2001 | Deininger et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,231,581 B1 | 5/2001 | Shank et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,299,607 B1 | 10/2001 | Osborn, III et al. |
| 6,306,079 B1 | 10/2001 | Trabucco |
| 6,312,448 B1 | 11/2001 | Bonutti |
| 6,319,262 B1 | 11/2001 | Bates et al. |
| 6,319,272 B1 | 11/2001 | Brenneman et al. |
| 6,322,492 B1 | 11/2001 | Kovac |
| 6,328,686 B1 | 12/2001 | Kovac |
| 6,328,758 B1 | 12/2001 | Tornier et al. |
| 6,334,446 B1 | 1/2002 | Beyar |
| 6,355,065 B1 | 3/2002 | Gabbay |
| 6,382,214 B1 | 5/2002 | Raz et al. |
| 6,387,040 B1 | 5/2002 | Grant et al. |
| 6,387,041 B1 | 5/2002 | Harari et al. |
| 6,391,060 B1 | 5/2002 | Ory et al. |
| 6,402,767 B1 | 6/2002 | Nash et al. |
| 6,406,234 B2 | 6/2002 | Frigg |
| 6,406,423 B1 | 6/2002 | Scetbon |
| 6,406,480 B1 | 6/2002 | Beyar et al. |
| 6,416,462 B1 | 7/2002 | Tovey et al. |
| 6,423,080 B1 | 7/2002 | Gellman et al. |
| 6,428,562 B2 | 8/2002 | Bonutti |
| 6,443,886 B2 | 9/2002 | Deininger et al. |
| 6,447,524 B1 | 9/2002 | Knodel et al. |
| 6,451,032 B1 | 9/2002 | Ory et al. |
| 6,461,291 B1 | 10/2002 | Polyak et al. |
| 6,475,139 B1 | 11/2002 | Miller |
| 6,478,727 B2 | 11/2002 | Scetbon |
| 6,478,763 B1 | 11/2002 | Simonsen et al. |
| 6,491,703 B1 | 12/2002 | Ulmsten |
| 6,494,879 B2 | 12/2002 | Lennox et al. |
| 6,517,566 B1 | 2/2003 | Hovland et al. |
| 6,530,879 B1 | 3/2003 | Adamkiewicz |
| 6,582,442 B2 | 6/2003 | Cabak et al. |
| 6,589,277 B1 | 7/2003 | Fabiani et al. |
| 6,595,911 B2 | 7/2003 | LoVuolo |
| 6,596,002 B2 | 7/2003 | Therin et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,685,629 B2 | 2/2004 | Therin |
| 6,692,491 B1 | 2/2004 | Phan |
| 6,702,827 B1 | 3/2004 | Lund et al. |
| 6,755,781 B2 | 6/2004 | Gellman |
| 6,802,807 B2 | 10/2004 | Anderson et al. |
| 6,830,052 B2 | 12/2004 | Carter |
| 6,908,425 B2 | 6/2005 | Luscombe |
| 6,936,052 B2 * | 8/2005 | Gellman et al. ............... 606/99 |
| 6,953,428 B2 | 10/2005 | Gellman et al. |
| 6,991,597 B2 | 1/2006 | Gellman et al. |
| 7,025,772 B2 | 4/2006 | Gellman et al. |
| 7,235,043 B2 | 6/2007 | Gellman et al. |
| 7,402,133 B2 * | 7/2008 | Chu et al. ............... 600/30 |
| 1,030,530 A1 | 6/2012 | Palmer |
| 1,066,025 A1 | 7/2013 | Lieberknecht |
| 2001/0018549 A1 | 8/2001 | Scetbon |
| 2001/0049467 A1 | 12/2001 | Lehe et al. |
| 2002/0022841 A1 | 2/2002 | Kovac |
| 2002/0028980 A1 | 3/2002 | Thierfelder et al. |
| 2002/0052654 A1 | 5/2002 | Darois et al. |
| 2002/0055748 A1 | 5/2002 | Gellman et al. |
| 2002/0068948 A1 | 6/2002 | Stormby et al. |
| 2002/0072694 A1 | 6/2002 | Snitkin et al. |

(56) References Cited

U.S. PATENT DOCUMENTS

| | | | |
|---|---|---|---|
| 2002/0077526 | A1 | 6/2002 | Kammerer et al. |
| 2002/0091298 | A1 | 7/2002 | Landgrebe |
| 2002/0091373 | A1 | 7/2002 | Berger |
| 2002/0099258 | A1 | 7/2002 | Staskin et al. |
| 2002/0099259 | A1 | 7/2002 | Anderson et al. |
| 2002/0107430 | A1 | 8/2002 | Neisz et al. |
| 2002/0116025 | A1 | 8/2002 | Haab |
| 2002/0128670 | A1 | 9/2002 | Ulmsten et al. |
| 2002/0138025 | A1 | 9/2002 | Gellman et al. |
| 2002/0143234 | A1 | 10/2002 | LoVuolo |
| 2002/0147382 | A1 | 10/2002 | Neisz et al. |
| 2002/0151762 | A1 | 10/2002 | Rocheleau et al. |
| 2002/0151909 | A1 | 10/2002 | Gellman et al. |
| 2002/0151910 | A1 | 10/2002 | Gellman et al. |
| 2002/0156489 | A1 | 10/2002 | Gellman et al. |
| 2002/0161382 | A1 | 10/2002 | Neisz et al. |
| 2002/0165566 | A1 | 11/2002 | Ulmsten |
| 2002/0188169 | A1 | 12/2002 | Kammerer et al. |
| 2003/0004395 | A1 | 1/2003 | Therin |
| 2003/0004580 | A1 | 1/2003 | Sump et al. |
| 2003/0009181 | A1 | 1/2003 | Gellman et al. |
| 2003/0010929 | A1 | 1/2003 | Priewe et al. |
| 2003/0023135 | A1 | 1/2003 | Ulmsten et al. |
| 2003/0023136 | A1 | 1/2003 | Raz et al. |
| 2003/0023137 | A1 | 1/2003 | Gellman |
| 2003/0023138 | A1 | 1/2003 | Luscombe |
| 2003/0028075 | A1 | 2/2003 | Ulmsten et al. |
| 2003/0045774 | A1 | 3/2003 | Staskin et al. |
| 2003/0050530 | A1 | 3/2003 | Neisz et al. |
| 2003/0062052 | A1 | 4/2003 | Carter et al. |
| 2003/0065402 | A1 | 4/2003 | Anderson et al. |
| 2003/0100954 | A1 | 5/2003 | Schuldt-Hempe et al. |
| 2003/0130670 | A1 | 7/2003 | Anderson et al. |
| 2003/0171644 | A1 | 9/2003 | Anderson et al. |
| 2004/0015048 | A1 | 1/2004 | Neisz et al. |

FOREIGN PATENT DOCUMENTS

| | | |
|---|---|---|
| DE | 24 28 319 | 1/1976 |
| DE | 25 32 242 | 2/1977 |
| DE | 8203923 | 4/1983 |
| DE | 32 06 846 | 9/1983 |
| DE | 33 40 581 | 6/1985 |
| DE | 35 21 717 | 12/1985 |
| DE | 34 40 889 | 6/1986 |
| DE | 86 04 065 U1 | 7/1986 |
| DE | 36 03 344 | 8/1986 |
| DE | 87 07 515 U1 | 9/1987 |
| DE | 37 09 706 | 10/1987 |
| DE | 87 07 516 U1 | 10/1987 |
| DE | 37 14 560 | 11/1987 |
| DE | 37 04 094 | 8/1988 |
| DE | 37 09 067 | 9/1988 |
| DE | 37 39 254 | 6/1989 |
| DE | 40 24 636 | 2/1992 |
| DE | 41 31 176 | 4/1993 |
| DE | 42 12 430 | 10/1993 |
| DE | 20204669 | 9/2003 |
| EP | 0 140 557 A3 | 5/1985 |
| EP | 0 153 831 A3 | 9/1985 |
| EP | 0 160 870 | 11/1985 |
| EP | 0 241 240 A2 | 10/1987 |
| EP | 0 281 763 A2 | 9/1988 |
| EP | 0 334 046 B1 | 9/1989 |
| EP | 0 337 918 B1 | 10/1989 |
| EP | 0 417 031 A2 | 3/1991 |
| EP | 0 437 063 A2 | 7/1991 |
| EP | 0 437 063 A3 | 7/1991 |
| EP | 0 450 608 | 10/1991 |
| EP | 0 484 671 A2 | 5/1992 |
| EP | 0 538 984 B1 | 4/1993 |
| EP | 0 555 103 | 8/1993 |
| EP | 0 558 993 A2 | 9/1993 |
| EP | 0 565 049 | 10/1993 |
| EP | 0 571 057 | 11/1993 |
| EP | 0 598 607 A2 | 5/1994 |
| EP | 0 599 772 A1 | 6/1994 |
| EP | 0 686 373 A1 | 12/1995 |
| EP | 0 854 691 | 7/1998 |
| EP | 0 778 749 | 12/2000 |
| EP | 0677297 | 12/2000 |
| EP | 1 151 722 A2 | 7/2001 |
| EP | 1 159 921 A2 | 12/2001 |
| EP | 1 151 722 A3 | 1/2002 |
| EP | 1191902 B1 | 4/2002 |
| FR | 2 432 861 | 3/1980 |
| FR | 2 718 012 | 10/1995 |
| FR | 2 739 016 | 3/1997 |
| GB | 2 151 142 A | 7/1985 |
| GB | 2 214 814 A | 9/1989 |
| GB | 2 268 690 A | 1/1994 |
| GB | 2 353 220 | 2/2001 |
| GB | 2 359 256 | 8/2001 |
| JP | 61-9601 | 11/1983 |
| JP | 63-095945 | 4/1988 |
| JP | 63-197443 | 8/1988 |
| JP | 6-114067 | 4/1994 |
| SE | 503 271 | 3/1996 |
| SE | 506164 | 4/1997 |
| SU | 990 220 A | 1/1983 |
| WO | WO 88/01853 | 3/1988 |
| WO | WO 89/04674 A | 6/1989 |
| WO | WO 89/10096 | 11/1989 |
| WO | WO 91/02493 | 3/1991 |
| WO | WO 92/05825 | 4/1992 |
| WO | WO 92/16152 | 10/1992 |
| WO | WO 92/21298 | 12/1992 |
| WO | WO 93/10715 | 6/1993 |
| WO | WO 93/10731 | 6/1993 |
| WO | WO 93/19678 | 10/1993 |
| WO | WO 94/04080 | 3/1994 |
| WO | WO 94/05223 | 3/1994 |
| WO | WO 94/19029 | 9/1994 |
| WO | WO 94/28799 | 12/1994 |
| WO | WO 95/05129 | 2/1995 |
| WO | WO 96/06567 | 3/1996 |
| WO | WO 96/25887 | 8/1996 |
| WO | WO 96/28100 | 9/1996 |
| WO | WO 97/06731 | 2/1997 |
| WO | WO-97/13465 | 4/1997 |
| WO | WO 97/30638 | 8/1997 |
| WO | WO 97/41792 | 11/1997 |
| WO | WO 97/43982 | 11/1997 |
| WO | WO 98/12971 | 4/1998 |
| WO | WO 98/35632 | 8/1998 |
| WO | WO 00/66030 | 11/2000 |
| WO | WO 00/74594 | 12/2000 |
| WO | WO 00/74613 | 12/2000 |
| WO | WO-00/74633 | 12/2000 |
| WO | WO 01/52750 | 7/2001 |
| WO | WO 02/19945 | 3/2002 |
| WO | WO 02/28315 | 4/2002 |
| WO | WO 03/007847 | 1/2003 |

OTHER PUBLICATIONS

Delorme., "La bandelette trans-obturatrice: un procede mini-invasif pour traiter l'incontinence urinaire d'effort de la femme," Progres en Urologie, vol. 11, 2001, pp. 1306-1313. (English summary therein).

Fianu et al., "Absorbable Polyglactin Mesh for Retropubic Sling Operations in Female Urinary Stress Incontinence," Gynecol. Obstet. Invest. vol. 16, pp. 45-50 (1983).

Giesy et al., "Ureteral Instrumentation: A New System for Continued Access via a Safety Guidewire," The Journal of Urology, No. 4, Part 2, Apr. 1988, p. 282A.

Gittes et al., No-Incision Pubovaginal Suspension for Stress Incontinence, Journal of Urology, vol. 138, Sep. 1987, pp. 568-570.

Haab et al. "Feasibility of Outpatient Percutaneous Bladder Neck Suspension Under Local Anesthesia," Urology, vol. 50, 1997, pp. 585-587.

Jacquetin, B., "Utilisation du TVT dans la chirurgie de l'incontinence urinaire féminine", J Gynecol Obste Biot Reprod 2000, vol. 29, pp. 242-247. (English summary therein).

(56) References Cited

OTHER PUBLICATIONS

Kersey et al., "The Gauze Hammock Sling Operation in the Treatment of Stress Incontinence," British Journal of Obstetrics and Gynecology, vol. 90, pp. 945-949, Oct. 1983.

Kovac et al., "Pubic Bone Suburethral Stabilization Sling for Recurrent Urinary Incontinence," Obstetrics & Gynecology, Apr. 1997, vol. 89, No. 4, pp. 624-627.

Norris et al, "Use of Synthetic Material in Sling Surgery: A Minimally Invasive Approach," Journal of Endourology, vol. 10, No. 3, Jun. 1996.

Petros, P., "An Integral Theory of Bladder Neck Opening, Closure and Urinary Incontinence in the Female", International Journal of Gynecology & Obstetrics, XXIII World Congress of Gynaecology and Obstetrics (FIGO) 1991.

Petros et al., "An Integral Theory and Its Method for the Diagnosis and Management of Female Urinary Incontinence," Scandinavian Journal of Urology and Nephrology, Supplement 153, 1993, pp. 1-93.

Petros, "Ambulatory Surgery for Urinary Incontinence and Vaginal Prolapse," The Medical Journal of Australia, Jul. 1994, vol. 161, pp. 171-172.

Petros et al., "Urethral Pressure Increase on Effort Originates From Within the Urethra, and Continence From Mulculovaginal Closure", Neurourology and Urodynamics, 1995, pp. 337-350.

Petros, "The Intravaginal Slingplasty Operation, a Minimally Invasive Technique for Cure of Urinary Incontinence in the Female," Aust. and N.Z. Journal of Obstetrics and Gynecology, 1996, vol. 4, pp. 453-461.

Petros, "Medium-term Follow-up of the Intravaginal Slingplasty Operation Indicates Minimal Deterioration of Urinary Continence With Time", Aust. and N.Z. Journal of Obstetrics and Gynecology, 1999, vol. 39, pp. 354-356.

Raz, "Modified Bladder Neck Suspension for Female Stress incontinence," Urology, Jan. 1981, vol. 17, No. 1, pp. 82-85.

Raz et al. "Fascial Sling to Correct Male Neurogenic Sphincter Incompetence: The McGuire/Raz Approach," The Journal of Urology, vol. 139, 1988, pp. 528-531.

Raz et al. "Vaginal Wall Sling" The Journal of Urology, vol. 141:1, Jan. 1989, pp. 43-46.

Stamey, "Endoscopic Suspension of the Vesical Neck for Urinary Incontinence," Surgery, Gynecology & Obstetrics, Apr. 1973, vol. 136, No. 4, pp. 547-554.

Stamey, "Endoscopic Suspension of the Vesical Neck for Urinary Incontinence in Females," Ann. Surg., Oct. 1980, vol. 192, No. 4, pp. 465-471.

Stamey, "Endoscopic Suspension of the Vesical Neck," Stanton, Tanagho (eds). Surgery of Female Incontinence. Springer-Verlag, Berlin; 1986, pp. 115-132.

Staskin, "Sling Surgery for the Treatment of Female Stress Incontinence," Problems in Urology, vol. 5, No. 1, Mar. 1991, pp. 106-122.

Staskin et al., "The Gore-tex sling procedure for female sphincteric incontinence: indications, technique, and results," World Journal of Urology, vol. 15, No. 5, 1997, pp. 295-299.

Sussman et al., "The Raz Bladder Neck Suspension: Five-Year Experience", The Journal of Urology, 1993, vol. 145, p. 223A.

Ulmsten et al., "Connective Tissue Factors in the Aetiology of Female Pelvic Disorders", Ann. Med., Dec. 1990, vol. 22, No. 6, p. 3.

Ulmsten et al., "Surgery for Female Urinary Incontinence", Current Opinion in Obstetrics & Gynecology, 1992, vol. 4, No. 3, pp. 456-462.

Ulmsten, et al, "Intravaginal Slingplasty", Zentralblatt für Gynäkologie, 1994, pp. 398-404.

Ulmsten et al., "Intravaginal Slingplasty (IVS): An Ambulatory Surgical Procedure for Treatment of Female Urinary Incontinence", Scandinavian Journal of Urology and Nephrology, Mar. 1995, vol. 29, No. 1, pp. 75-82.

Ulmsten et al., "An Ambulatory Surgical Procedure Under Local Anesthesia for Treatment of Female Urinary Incontinence", The International Urogynecology Journal, 1996, pp. 81-86.

Ulmsten et al., "A Multicenter Study of Tension-Free Vaginal Tape (TVT) for Surgical Treatment of Stress Urinary Incontinence", International Urogynecology Journal, 1998, vol. 9, No. 4, pp. 210-213.

Ulmsten et al., "A Three-Year Follow Up of Tension Free Vaginal Tape for Surgical Treatment of Female Stress Urinary Incontinence", British Journal of Obstetrics and Gynaecology, Apr. 1999, vol. 106, pp. 345-350.

Ulmsten, U., "An Introduction to Tension-Free Vaginal Tape (TVT)—A New Surgical Procedure for Treatment of Female Urinary Incontinence", International Urogynecology Journal, 2001, vol. 12, Suppl. 2, pp. S3-S4.

Ulmsten, U., "The Basic Understanding and Clinical Results of Tension-Free Vaginal Tape for Stress Urinary Incontinence", Der Urologe [A] Apr. 2001, pp. 269-273.

International Search Report from International Application No. PCT/US03/25451 dated Jan. 16, 2004.

Adamiak et al., "The Efficacy and Safety of the Tension-Free Vaginal Tape Procedure Do Not Depend on the Method of Analgesia", European Urology, 2002, vol. 42, pp. 29-33.

Agarwala et al., "Minimally invasive management of urinary incontinence", Current Opinion in Obstetrics and Gynecology, 2002, vol. 14, No. 4, pp. 429-433.

Amid, Parviz K., et al., "Experimental evaluation of a new composite mesh with the selective property of incorporation to the abdominal wall without adhering to the intestines", Journal of Biomedical Materials Research, vol. 28, pp. 373-375 (1994).

Araki et al., "The Loop-Loosening Procedure for Urination Difficulties after Stamey Suspension of the Vesical Neck," The Journal of Urology, Aug. 1990, vol. 144, pp. 319-323.

Beck et al., "A 25-Year Experience with 519 Anterior Colporrhaphy Procedures," Obstetrics & Gynecology, Dec. 1991. vol. 78, No. 6, pp. 1011-1018.

Blaivas, "Successful Pubovaginal Sling Surgery," Contemporary Urology, Jul. 1993, pp. 40-63.

Blaivas, "Pubovaginal Fascial Sling for the Treatment of Complicated Stress Urinary Incontinence," The Journal of Urology, Jun. 1991, vol. 145, pp. 1214-1218.

Benderev, "A Modified Percutaneous Outpatient Bladder Neck Suspension System," The Journal of Urology, Dec. 1994, vol. 152, pp. 2316-2320.

Benderev, "A New Endoscopic Bladder Neck Suspension for the Outpatient Treatment of Stress urinary Incontinence," The Journal of Urology, Apr. 1993, No. 4, videotape, V-40, p. 197A.

Benderev, "Anchor Fixation and Other Modifications of Endoscopic Bladder Neck Suspension," Urology, Nov. 1992, vol. 40, No. 5, pp. 409-418.

Brenner, "Mesh Materials in Hernia Repair," Expert Meeting on Hernia Surgery, St Moritz, 1994. Basel Karger, 1995, pp. 172-179.

Carachi, R., et al., "Copllagen-Coated Vicryl Mesh: A New Bioprosthesis in Pediatric Surgical Practice", Journal of Pediatric Surgery, vol. 30, No. 9 pp. 1302-1305 (1995).

Cruikshank," Reconstructive Procedures for the Gynecologic Surgeon," American Journal of Obstetrics and Gynecology, Feb. 1993, vol. 168, No. 2, pp. 469-475.

DeLancey, "Structural Support of the Urethra as it Relates to Stress urinary Incontinence: The Hammock Hypothesis," American Journal of Obstetrics and Gynecology, Jun. 1994, vol. 170, No. 6, pp. 1713-1723.

Falconer et al., "Clinical Outcome and Changes in Connective Tissue Metabolism after Intravaginal Slingplasty in Stress Incontinent Women," The International Urogynecology Journal, 1996, vol. 7,133-137.

Falk et al., United States Statutory Invention Registration, Reg. No. H1028, Mar. 3, 1992, United States Patent Office, Washington D.C.

Fianu et al., "Absorbable Polyglactin Mesh for Retropubic Sling Operations in Female Urinary Stress Incontinence", Gynecol. Obstet, Invest., 1983, vol. 16, pp. 45-50.

Forneret et al., "Cost-Effective Treatment of Female Stress Urinary Incontinence: Modified Pereyra Bladder Neck Suspension," Urology, Apr. 1985, vol. 25, No. 4, pp. 365-367.

Hancock et a)., "Transpubic Suspension of the Bladder Neck for Urinary Incontinence," The Journal of Urology, May 1980, vol. 123, pp. 667-668.

(56) References Cited

OTHER PUBLICATIONS

Henriksson et al., "A Urodynamic Comparison between Abdominal Urethrocystopexy and Vaginal Sling Plasty in Female Stress Incontinence", Urologia International's, 1978, vol. 33, No. 1-3, pp. 111-116.
Henriksson, et al., "A urodynamic evaluation of the effects of abdominal urethrocystopexy and vaginal sling urethroplasty in women with stress incontinence", American Journal of Obstetrics and Gynecology, 1978, vol. 131, No. 1, pp. 77-82.
Hoffman et al., Transvestibular Retropubic Bladder Neck Suspension: A Pilot Study, The Journal of Reproductive Medicine, Mar. 1995, vol. 40, No. 3, pp. 181-184.
Iglesia et al., "The Use of Mesh in Gynecologic Surgery," International Urogynecology Journal, 1997, vol. 8, pp. 105-115.
Iosif et al., "Urodynamic studies of women with prolapse and stress incontinence before and after surgical repair", Zentralblatt fur Gynakologie, 1979, vol. 101, pp. 1433-1442.
Leach et al., "Percutaneous Bladder Neck Suspension," Urologic Clincs of North America, Aug. 1996, vol. 23, No. 3, pp. 511-516.
Leach, "Bone Fixation Technique for Transvaginal Needle Suspension", Urology, May 1988, vol. 31, No. 5, pp. 388-390.
Leach et al., "Modified Pereyra Bladder Neck Suspension after Previously Failed Anti-Incontinence Surgery," Urology, Apr. 1984, vol. 23, No. 4, pp. 359-362.
Mascio, et al., "Therapy of Urinary Stress Incontinence in Women Using Mitek Gil Anchors," The Mitek Brochure, 1993.
Mattox et al., "Modification of the Miya Hook in Vaginal Colpopexy," The Journal of Reproductive Medicine, Oct. 1995, vol. 40, No. 10, pp. 681-683.
McKiel et al., Marshall-Marchetti Procedure: Modification, The Journal of Urology, 1966, vol. 96, pp. 737-739.
Mitchell, et al., "Hook Needle and Retractor for Posterior Urethroplasty," British Journal of Urology, 1970, vol. 42, pp. 599-600.
Nativ et al., "Bladder Neck Suspension Using Bone Anchors for the Treatment of Female Stress Incontinence," ASAIO Journal, 1997, pp. 204-208.
Nichols et al., "Identification of Pubourethral Ligaments and their Role in Transvaginal Surgical Correction of Stress Incontinence," American Journal of Obstetrics and Gynecology, Jan. 1973, vol. 115, No. I, pp. 123-128.
Pereyra, "A Simplified Surgical Procedure for the Correction of Stress Incontinence in Women," The Journal of Urology, Feb. 2002, vol. 167, pp. 1116-1118.
Petros et al., "The Autogenic Ligament Procedure: A Technique for Planned Formation of an Artificial Neo-Ligament", Acta Obstetricia et Gynecologica Scandinavica, 1990, vol. 69, Supplement 153, pp. 43-51.
Petros et al., "The Tuck Procedure: A Simplified Vaginal Repair for Treatment of Female Urinary Incontinence", Acta Obstetricia et Gynecologica Scandinavica, 1990, vol. 69, Supp. 153, pp. 41-42.
Rezapour et al., "Tension-Free Vaginal Tape (TVT) in Woman with Recurrent Stress Urinary Incontinence—A Long-term Follow up", International Urogynecology Journal, 2001, vol. 12 (Suppl 2), pp. S9-S11.
Riachi et al., "Repeat Tension-Free Transvaginal Tape (TVT) Sling for the Treatment of Recurrent Stress Urinary Incontinence", International Urogynecology Journal, 2002, vol. 13, No, 2, pp. 133-135.
Richardson et al., Treatment of Stress Urinary Incontinence Due to Paravaginal Fascial Defect, Obstetrics & Gynecology, Mar. 1981, vol. 57, No. 3, pp. 357-362.
Richmond et al., "Modification of the Bankan Reconstruction with a Suture Anchor," The American Journal of Sports Medicine, 1991, vol. 19, No. 4, pp. 343-346.
Robertson et al., "Soft Tissue Fixation to Bone," The American Journal of Sports Medicine, 1986, vol. 14, No. 5. pp. 398-403.
Schaeffer et.al., "Endoscopic Suspension of Vesical Neck for Urinary Incontinence," Urology, May 1984, vol. 23, No. 5, pp. 484-494.
Schatzker et al., "The Rationale of Operative Fracture Care," 1987, pp. XIV-XV and 159.
Scheuer, "The Modified Pereyra Bladder Neck Suspension Procedure Using Mitek Gil Anchors," The Mitek Brochure, 1993.
Spencer et al., "A Comparison of Endoscopic Suspension of the Vesical Neck with Suprapubic Vesicourethropexy for Treatment of Stress Urinary Incontinence," The journal of Urology, Mar. 1987, vol. 137, pp. 411-415.
Tension-Free Support for Incontinence, 1, 2, 3, 4, 5 Years of Proven Performance, Lasting freedom for your SUI patients, Gynecare TVT, 6 pgs. (2002).
The essence of a contemporary synthetic sling self-anchoring complete adjustability elastic, Safyretm Autofixation System, Promedon, 4 pgs. (2002).
Trockman et al.,"Modified Pereyra Bladder Neck Suspension: 10-Year Mean Follow Up Using Outcomes Analysis in 125 Patents," The Journal of Urology, Nov. 1995, vol. 154, pp. 1841-1847.
Urken, "About Lifecell—Our Science," Lifecell, 2001.
Vasavada et al., "Incisionless Pubovaginal Fascial Sling Using Transvaginal Bone Anchors for the Treatment of Stress Urinary Incontinence," Digital Urology Journal, 2001.
Wang et al., "Tension-Free Vaginal Tape, A Minimally Invasive Solution to Stress Urinary Incontinence in Women", The Journal of Reproductive Medicine, May 1998, vol. 43, No. 5, pp. 429-434.
Webster, "Female Urinary Incontinence," Urologic Surgery, 1983, Third Edition, pp. 665-679.
Webster et al., "Voiding Dysfunction Follow-up Cystourethropexy: Its Evaluation and Management," The Journal of Urology, Sep. 1990, vol. 144, pp. 670-673.
Winter, "Peripubic Urethropexy for Urinary Stress Incontinence in Women," Urology, Oct. 1982, vol. 20, No. 4, pp. 408-411.
Zimmern et al., "A Prospective Evaluation of Four-Corner Bladder Neck Suspension for Grade II/III Cystocele Repair," Neurology and Urodynamics, 1990, vol. 9, pp. 195 and 231.
Zimmern et al., "Transvaginal Closure of the Bladder Neck," Seminars in Urology, Feb. 1986, vol. 4, No. 1, pp. 30-32.
Zacharin, "Abdominoperineal Urethral Suspension in the Management of Recurrent Stress Incontinence of Urine—A 15-Year Experience," Obstetrics & Gynecology, Nov. 1983, vol. 62, No. 5, pp. 644-654.
A Superior Approach to Tensionless Sling Placement, SPARC sling system for stress urinary incontinence, American Medical Systems, Inc., 4 pages. (2001).

\* cited by examiner

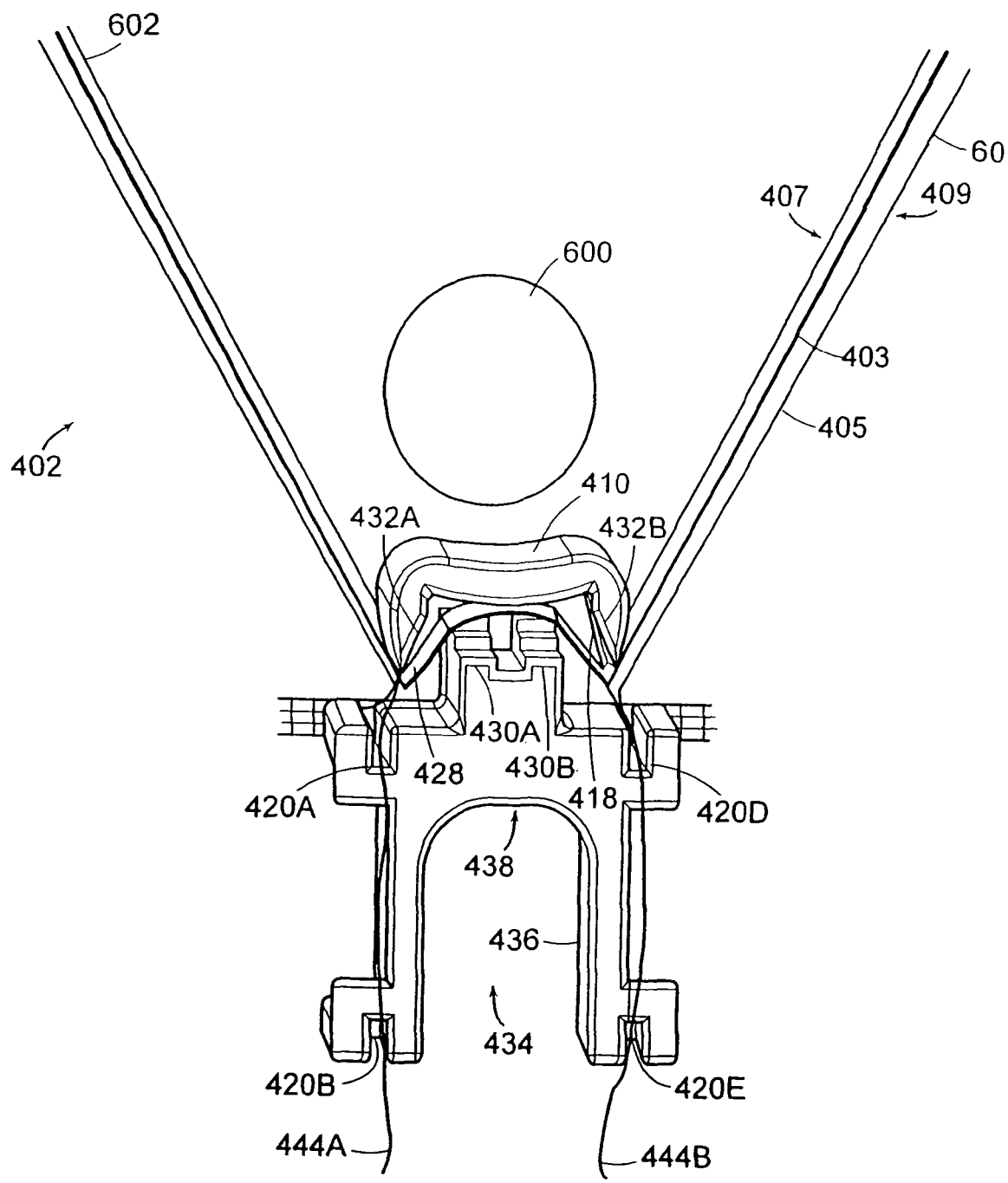

SPACER FOR SLING DELIVERY SYSTEM

RELATED APPLICATIONS

This application is a continuation of U.S. patent application Ser. No. 10/641,376, filed on Aug. 14, 2003, now U.S. Pat. No. 7,402,133, which claims the benefit of and priority to provisional patent application Ser. No. 60/434,167, filed Dec. 17, 2002, and provisional patent application Ser. No. 60/449,465, filed Feb. 24, 2003, the entirety of which is incorporated herein by reference.

TECHNICAL FIELD

The invention relates generally to systems, and related methods and devices, for delivering an implant, such as a surgical sling, to an anatomical site in the body of a patient.

BACKGROUND OF THE INVENTION

Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

Improved systems and methods for treating SUI are needed.

SUMMARY OF THE INVENTION

The invention addresses deficiencies of the prior art by providing devices and methods for facilitating spacing away from a sling a sleeve, which at least partially encloses the sling. Such sling/sleeve configurations may be implanted into a patient's body, for example, for the treatment of urinary incontinence. According to a particular embodiment, the sling/sleeve combination is delivered to a mid-urethral location of a patient. The methods and systems of the invention simplify cutting the sleeve at an intermediate location by a medical operator, while also reducing the likelihood of the medical operator inadvertently cutting the sling. Once the sleeve is cut at an intermediate location, preferably via the vagina, the sleeve may be removed from the patient, for example, by pulling on sleeve ends. According to another advantage, the systems and methods of the invention space an intermediately located portion of the sling away from patient tissue, such as periurethral tissue, to make it easier for a medical operator to position the sling/sleeve combination without traumatizing the periurethral tissue.

The invention, which may be employed with any suitable sleeve/sling combination, in various aspects, features a spacer for positioning away from a portion of a sling a portion of a sleeve that at least partially encloses the sling; methods of making such a spacer; medical kits including such a spacer; and methods of treating a damaged, weakened, sagging, herniated, or prolapsed portion of a patient's body using such a spacer.

According to one embodiment of the invention, the spacer includes a tube having first and second ends and a lumen extending between the first and second ends. Preferably, the tube is formed into a V-shape, for example, by bending the tube at its midpoint such that the tube has first and second tube portions. When employed, the sleeve traverses through the lumen of the first and second tube portions and forms a sleeve bridge between the first and second tube ends across the open end of the V-shape. The tube can also include an aperture at the vertex of the first and second tube portions. The sleeve can pass, for example, into the lumen in the first tube section via the aperture, out the first tube end, into the second tube end, through the second tube section and out the aperture, thus forming the sleeve bridge between the first and second tube ends. The spacer can also include an anchoring mechanism for anchoring the sling in the tube. In some configurations, the anchoring mechanism includes a suture that passes through the lumen to form a suture bridge across the first and second tube ends. According to one feature, the spacer includes a truss extending between the first and second tube portions.

In another embodiment, the spacer can include a sling engaging member. The sling engaging member facilitates the positioning of a portion of a sling away from a portion of a sleeve. In one embodiment, the sling engaging member includes a slot for traversal by the sling. The sling slot can include an anchoring mechanism for holding the sling such that the sling does not move during placement of the sling at a site in the body. The anchoring mechanism can be, for example, teeth such as tapered teeth or a cantilever beam such as a beam having an inverted T-shape.

The spacer may also include a sleeve engaging member. The sleeve engaging member facilitates the positioning of a portion of a sleeve away from a portion of a sling. In one embodiment, the sleeve engaging member includes a slot for traversal by the sleeve. The sleeve engaging member serves to hold the sleeve in a position away from the sling so that the medical operator can cut the sleeve without inadvertently also cutting the sling.

In some configurations, the spacer also includes a tissue spacing member for spacing the sling away from a patient's tissue. As mentioned above, such spacing makes it easier for a medical operator to position the sling during delivery. Preferably the tissue spacing member has a concave surface for supporting tissue, such as periurethral tissue at a mid-urethral location in a patient's body.

The spacer of the invention may include an indicator for indicating to the medical operator a direction in which the spacer is to be removed. The indicator can also include a handle for facilitating spacer removal. In one configuration, the indicator is shaped like an arrowhead, with the tip of the arrowhead indicating the direction of removable. In other configurations, the arrowhead is large enough to form a handle to facilitate spacer removal.

According to a further embodiment, the spacer of the invention includes a receptacle for traversal by a portion of the sleeve. The spacer may also include an insert for mating within the receptacle and holding the portion of the sleeve in place within the receptacle. The receptacle may be of any suitable shape. Preferably, it is substantially U-shaped and the insert is appropriately shaped for mating engagement with the receptacle.

In some embodiments, the spacer includes an elongated shaft extending between the sleeve engaging member and the sling engaging member. The presence of an elongated shaft in the spacer is advantageous as it facilitates spacing of the sleeve away from the sling and has the added feature of making it easier for a medical operator to remove the spacer from the patient's body following sling placement. In one embodiment, the elongated shaft includes a proximal end and a distal end and a channel extending between the proximal end and the distal end. The sling is positioned at the distal end of the elongated shaft and the sleeve is passed through the channel to the proximal end where a sleeve engaging member holds the sleeve in place, and/or forms a sleeve bridge to facilitate cutting of the sleeve by a medical operator.

In an alternative configuration the sling engaging member includes a pin extending from the spacer. In one such configuration, the spacer includes a first elongated shaft extending between the pin and the sleeve engaging member and a second elongated shaft extending between the pin and the sleeve engaging member, and the first and second elongated members each include a channel for passage of the sleeve. The distal ends of the elongated shafts further include a sleeve engaging member, for example, for holding the sleeve in place and/or for forming a sleeve bridge for facilitating cutting of the sleeve by a medical operator.

In another aspect, the invention provides a sling delivery system including a sling assembly and a spacer, as described above. The sling assembly includes an elongated sling (i.e., a mesh sling) and a sleeve enclosing at least a portion of the sling. For example, a sling system can include a sling, a sleeve covering at least a portion of the sling, and a spacer, wherein the sleeve comprises first and second sides, the first side having first and second slit-shaped apertures intermediately located between first and second ends of the sleeve, the sling threads out of the sleeve through the first slit-shaped aperture and back into the sleeve through the second slit-shaped aperture creating a mid-length sleeve loop, and the spacer is positioned to space the sling away from the mid-length sleeve loop. In this embodiment, the spacer can be a tube, such as a substantially flat tube which includes an aperture for sighting a cutting line through the spacer and sleeve loop to separate the sleeve into portions that may be removed from about the sling, and wherein the sleeve loop is partially secured within the interior of the tube.

In one embodiment of this aspect of the invention, the sleeve includes first and second ends and the spacer is positioned intermediate to the first and second ends. In another embodiment, the sling includes first and second sides, the sleeve includes first and second sides, and the spacer is disposed between the second side of the sling and the second side of the sleeve. According to various configurations, the sling/sleeve combination may terminate in any suitable fashion.

The foregoing and other objects, aspects, features, and advantages of the invention will become more apparent from the following description.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 6B depicts a perspective side view of the illustrative spacer and sling assembly section of FIG. 6A after the sleeve bridge is cut.

ILLUSTRATIVE DESCRIPTION OF THE INVENTION

Figure 1:
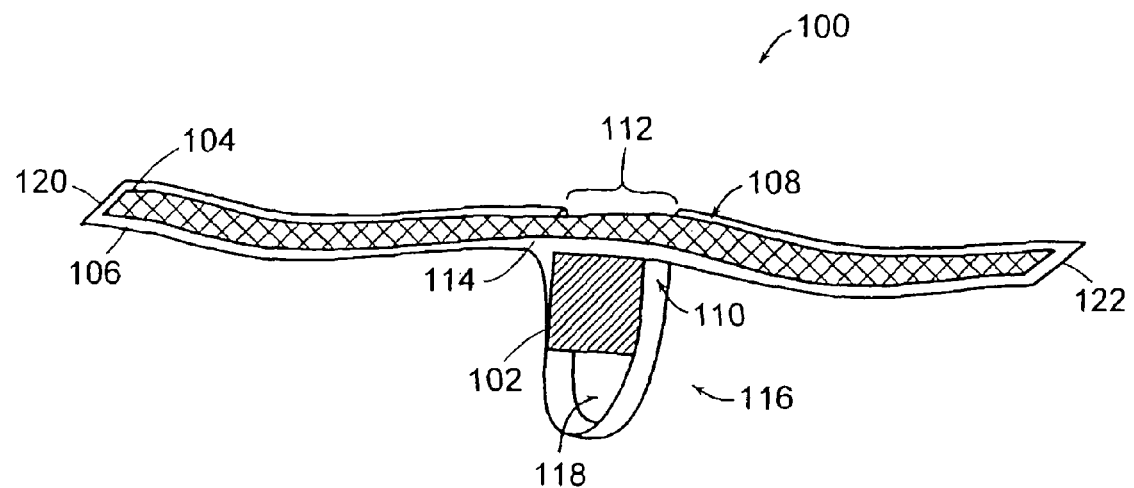
FIG. 1 depicts a perspective side view of a spacer according to an illustrative embodiment of the invention employed with an exemplary sling assembly section.

In general, the invention pertains to systems, methods, and devices relating to delivering a sling to an anatomical site in the body of a patient, for example, the periurethral tissues of the patient in the treatment of female urinary incontinence. More particularly, the invention is directed to various configurations of spacers for spacing away from the sling at least a portion of a sleeve that at least partially encloses the sling. By spacing a portion of the sleeve away from the sling, the spacers of the invention enable a medical operator to more easily cut the sleeve, without damaging the sling, so that the sleeve may be removed from a patient's body, while leaving the sling in place. Another feature of some spacer configurations of the invention is that the spacer acts to space a portion of the sling away from patient tissue, for example, periurethral tissue. By spacing a portion of the sling away from the patient tissue, the spacer of the invention makes it easier for the medical operator to position the sling without traumatizing patient tissue that would otherwise rub against the sling during positioning. As a preliminary matter it should be noted that the various illustrative spacer configurations discussed in further detail below may be employed with any suitable sling/sleeve configuration. By way of example, the spacers of the invention may be employed with sleeves having one or more apertures. They may also be employed with sleeves having a generally unitary construction or alternatively, with sleeves formed from multiple discrete sections. Without limitation, exemplary sling/sleeve configurations that may be operable with illustrative embodiments of the invention may be found in U.S. patent application entitled Medical Slings, to Rao et al Ser. No. 10/641,170, pending; U.S. patent application entitled Medical Slings, to Chu, Ser. No. 10/641,192, pending; U.S. provisional patent application entitled Surgical Slings, to Li et al, Ser. No. 60/495,439; U.S. patent applications entitled Systems, Methods and Devices relating to Delivery of Medical Implants, to Chu et al., Ser. Nos. 10/642,395, pending, 10/642,397, abandoned, 10/642,365, pending, and 10/641,487, now U.S. Pat. No. 7,364,541; U.S. patent application entitled Medical Implant, to Chu et al., Ser. No. 10/640,838, pending; U.S. provisional patent application Ser. No. 60/403,555; U.S. provisional patent application Ser. No. 60/465,722; U.S. patent application Ser. No. 10/460,112, now U.S. Pat. No. 7,070,558; and U.S. patent application Ser. No. 09/096,983, now U.S. Pat. No. 6,100,821, the entire contents of which are incorporated herein by reference.

As another preliminary matter, the ends of the slings or sleeves employed may terminate in any suitable configurations or structures such as loops, for example, apertures, male and female connectors, guide tubes and the like. Some exemplary sling/sleeve termination configurations and structures are disclosed in U.S. patent application Ser. No. 10/325,125; U.S. provisional patent application Ser. No. 60/418,827; U.S. provisional patent application Ser. No. 60/418,642; U.S. provisional patent application Ser. No. 60/434,167; and U.S. provisional patent application Ser. No. 60/403,555; the disclosures of which are incorporated herein by reference.

As a further preliminary matter, it should be noted that the various illustrative spacer configurations may be employed with any suitable sling delivery system. By way of example, the spacers of the invention may be employed with any sling/sleeve configurations and delivery systems appropriate for treating urinary incontinence. Such delivery systems include, for example, those delivery systems configured for suprapubic, pre-pubic, transvaginal or transobturator approaches. Without limitation, exemplary delivery systems, slings, sling attachments and methodologies that may be employed in combination with the spacers of the invention can be found in U.S. patent application Ser. No. 10/093,498; U.S. patent application Ser. No. 10/093,398; U.S. patent application Ser. No. 10/093,450; U.S. patent application Ser. No. 10/094,371; U.S. patent application Ser. No. 10/094,352; U.S. patent application Ser. No. 10/093,424; U.S. provisional patent application Ser. No. 60/403,555; U.S. patent application Ser. No. 09/916,983; U.S. provisional patent application Ser. No. 60/465,722; U.S. provisional patent application Ser. No. 60/418,827; U.S. provisional patent application Ser. No. 60/418,642; U.S. provisional patent application Ser. No. 60/274,843; U.S. provisional patent application Ser. No. 60/286,863; and U.S. provisional patent application Ser. No. 60/434,167, the disclosures of which are incorporated herein by reference.

Turning now to illustrative embodiments of the invention, FIG. 1 depicts a perspective side view of a spacer 102 according to an illustrative embodiment of the invention employed with an exemplary sling assembly section 100. As depicted, the sling assembly 100 includes a mesh sling 104 partially enclosed by a sleeve 106. Although, the sleeve 106 may be any suitable sleeve, illustratively it is shown as having a first sleeve wall 108 and a second sleeve wall 110, with the mesh sling 104 located between the first 108 and second 110 sleeve walls. The first sleeve wall 108 includes a discontinuity forming a gap 112 exposing an intermediate portion 114 of the mesh sling 104. The particular spacer 102 in this embodiment is generally rectangular in shape and spaces an intermediately located portion 116 of the sleeve wall 110 away from the intermediate sling portion 114. The spacer 102 is positioned to create a loop 118 in the intermediate portion 116 of the sleeve wall 110. As described below in further detail with regard to FIGS. 4-11, the spacer 102 can be operatively engaged with the intermediate portion 116 of the sleeve wall 110 in a variety of ways. By way of example, the spacer 102 may include any number of slots, channels or protuberances to engage the sleeve wall 110. Alternatively, the spacer 102 can be bonded to or interconnected via suture with the sleeve wall 110.

In operation, once the sling assembly 100 is positioned within the body of a patient, for example under a patient's mid-urethra, a medical operator can insert a pair of scissors into the loop 118 to cut the sleeve 106, without risking accidentally cutting the sling 104. With the sleeve 106 so cut, the sleeve ends 120 and 122 may be pulled to remove the sleeve 106 from the patient's body, while leaving the sling 104 in place. The spacer 102 may be removed, for example, via the patient's vagina.

Figure 2:
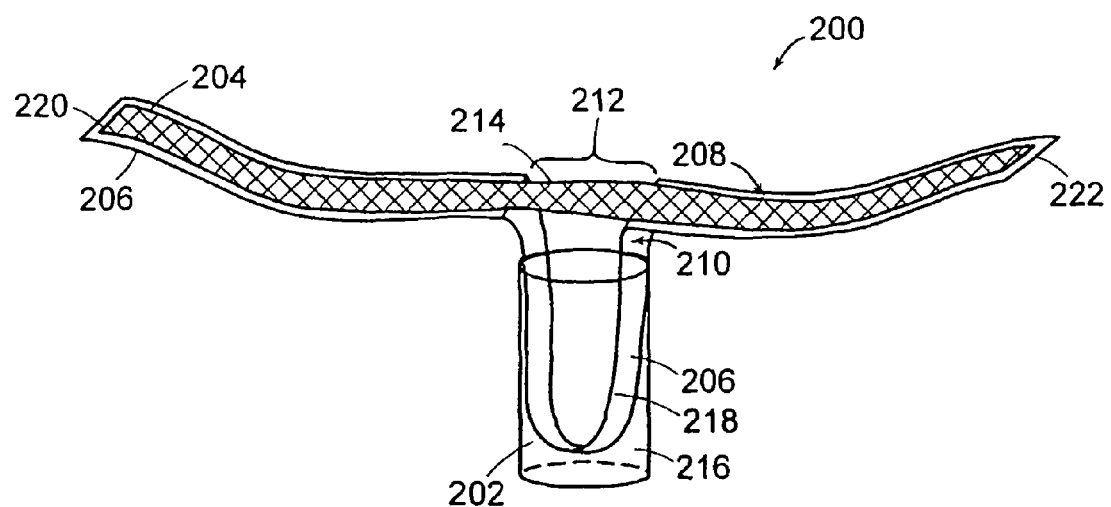
FIG. 2 depicts a perspective side view of a spacer according to another illustrative embodiment of the invention employed with an exemplary sling assembly section.

FIG. 2 depicts a perspective side view of a spacer 202 according to another illustrative embodiment of the invention employed with an exemplary sling assembly section 200. The illustrative spacer 202 of FIG. 2 is substantially cylindrical in shape. In a similar fashion to FIG. 1, the sling assembly 200 includes a mesh sling 204 partially enclosed by a sleeve 206. As in the case of the sleeve 106, the sleeve 206 may be any suitable sleeve. Illustratively, it is shown as having a first sleeve wall 208 and a second sleeve wall 210, with the mesh sling 204 located between the first 208 and second 210 sleeve walls. The first sleeve wall 208 includes a discontinuity forming a gap 212 exposing an intermediate portion 214 of the mesh sling 204. The particular spacer 202 is generally cylindrical in shape and spaces an intermediately located portion 216 of the sleeve wall 210 away from the intermediate sling portion 214. The spacer 202 is positioned to create a loop 218 in the intermediate portion 216 of the sleeve wall 210. As in the case of the embodiment of FIG. 1, and as described below in further detail with regard to FIGS. 4-11, the spacer 202 can be operatively engaged with the intermediate portion 216 of the sleeve wall 210 in a variety of ways. By way of example, the spacer 202 may include any number of slots, channels or protuberances to engage the sleeve wall 210. Alternatively, the spacer 202 can be bonded to or interconnected via suture with the sleeve wall 210. In some illustrative configurations, the spacer 202 is flattened to form a friction based attachment to a portion of the intermediate portion 216 of the sleeve wall 210.

Once the sling assembly 200 is positioned within the body of a patient, for example under a patient's mid-urethra, a medical operator can cut through the spacer 202 and thus, cut through the intermediate portion 216 of the sleeve wall 210, without risking accidentally cutting the sling 204. As in the case of the embodiment of FIG. 1, with the sleeve 206 so cut, the sleeve ends 220 and 222 may be pulled to remove the sleeve 206 from the patient's body, while leaving the sling 204 in place. The spacer 202 may be removed, for example, via the patient's vagina.

Figure 3A:
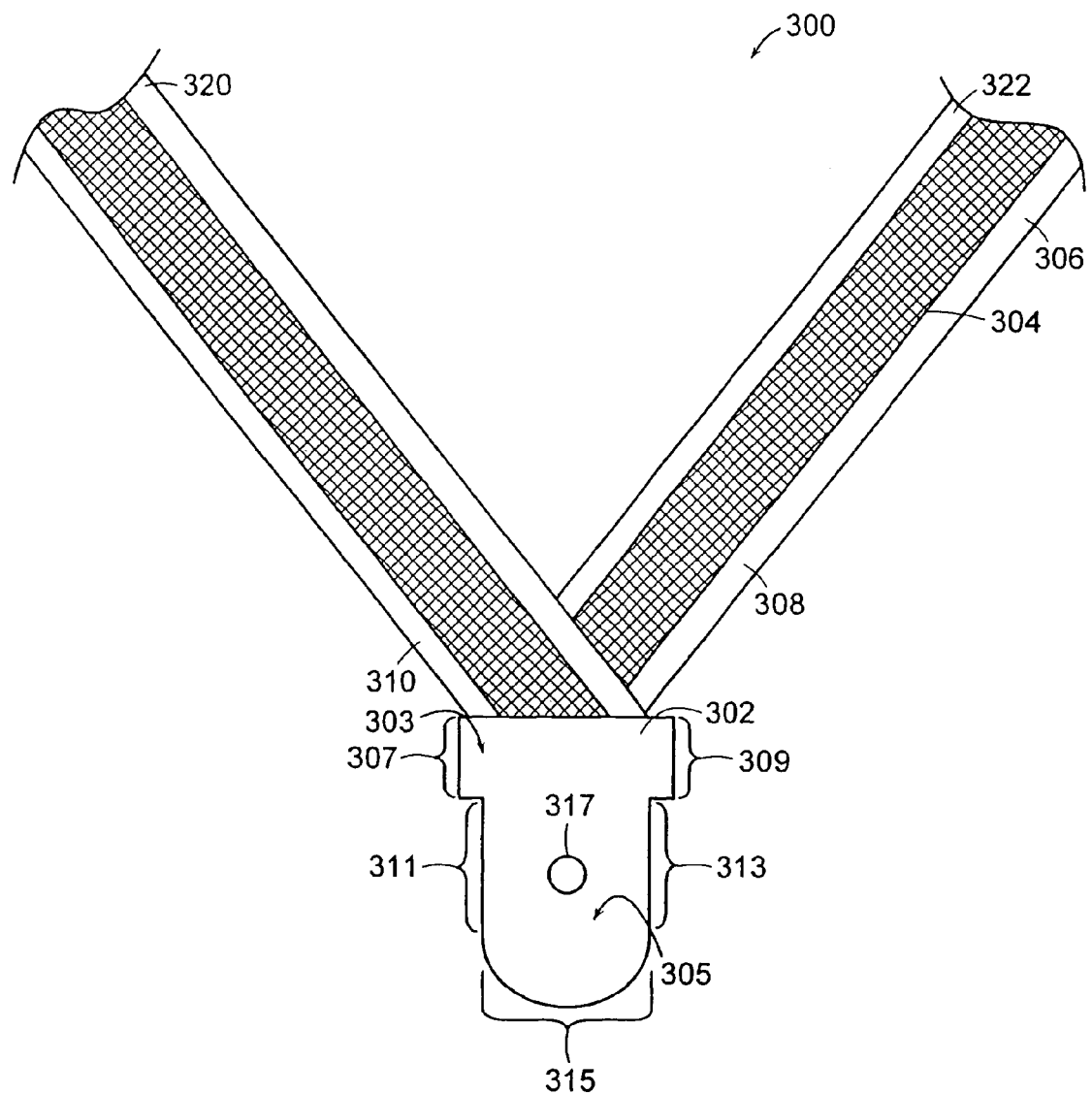
FIG. 3A depicts a perspective side view of a spacer according to another illustrative embodiment of the invention employed with an exemplary sling assembly section.
Figure 3B:
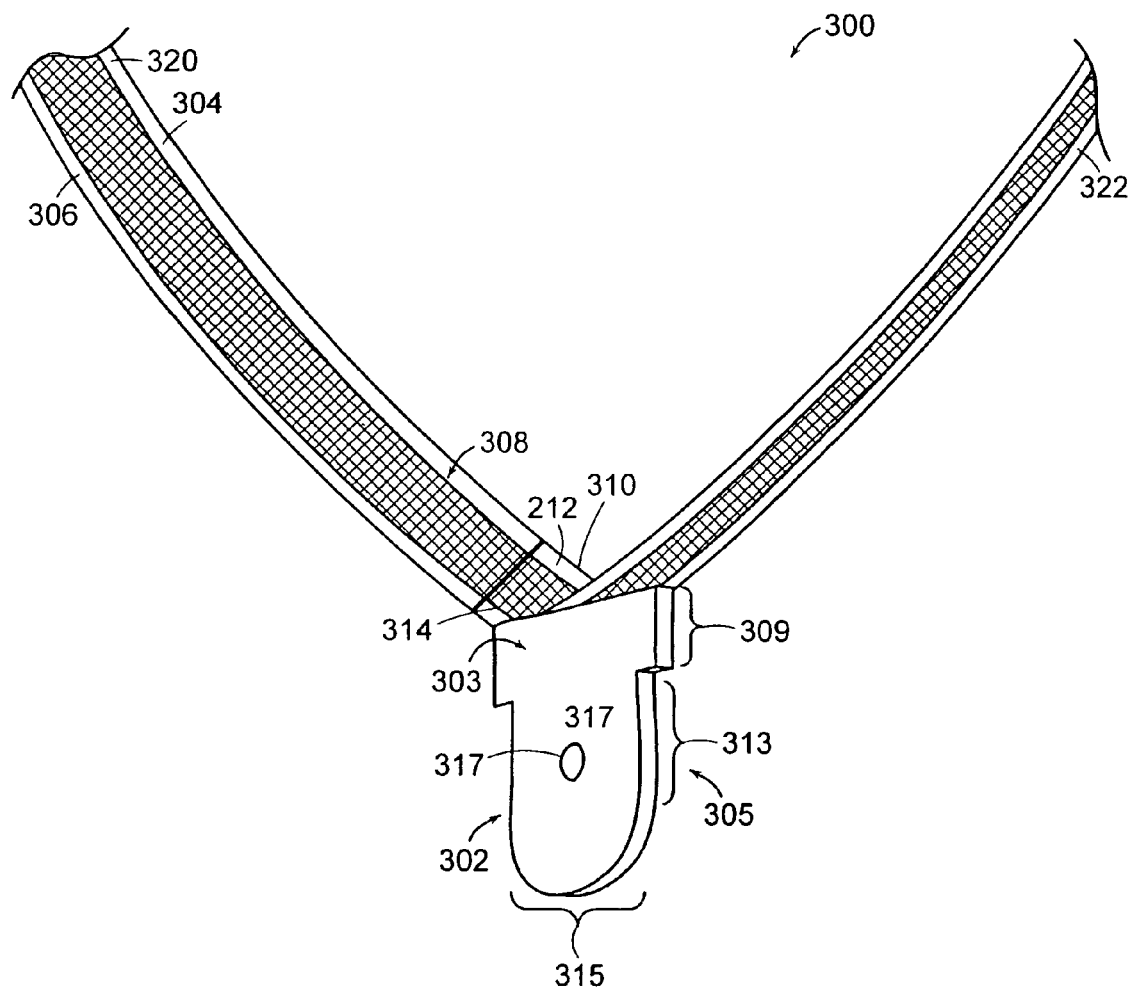
FIG. 3B depicts a perspective front view of the spacer and sling assembly section of FIG. 3A.

FIG. 3A depicts a perspective side view of a spacer 302 according to another illustrative embodiment of the invention employed with an exemplary sling assembly section 300, and FIG. 3B depicts a perspective front view of the spacer 302 and sling assembly section 300 of FIG. 3A. Referring to FIGS. 3A and 3B, in a similar fashion to the embodiments of FIGS. 1 and 2, the sling assembly 300 includes a mesh sling 304 partially enclosed by a sleeve 306. As in the case of the sleeve 206, the sleeve 306 may be any suitable sleeve. Illustratively, it is shown as having a first sleeve wall 308 and a second sleeve wall 310, with the mesh sling 304 located between the first 308 and second 310 sleeve walls. The first sleeve wall 308 includes a discontinuity forming a gap 312 exposing an intermediate portion 314 of the mesh sling 304.

The particular spacer 302 is generally flat in shape and includes first 303 and second 305 sides between which an intermediately located portion 316 (not visible) of the sleeve wall 310 is sandwiched and spaced away from the intermediate sling portion 314. According to the illustrative embodiment, the tab spacer 302 is closed along its top edges 307 and 309 and open along its intermediate edges 311 and 313. The bottom edge 315 is left open until after the intermediately located portion 316 of the sleeve wall 310 is inserted in between the first 303 and second 305 sides of the spacer 302. Subsequent to insertion of the intermediate portion 316, the bottom edge 315 of the spacer 302 is bonded, for example, using heat or glue, together and to that portion of the intermediate portion 316 of the sleeve wall 310 located near the bottom edge 315 of the spacer 302. With the bottom edge 315 so bonded, the spacer 302 may be removed by cutting from one intermediate edge 311 to the other intermediate edge 313, and then sliding the remaining portion of the spacer 302 off the intermediate portion 316 of the sleeve wall 310. The illustrative spacer 302 also includes an aperture 317, which indicates a location for making the cut between the intermediate edges 311 and 313. The aperture 317 also enables a person to view the intermediate portion 316 of the sleeve wall 310 to verify proper installation into the spacer 302.

Once the sling assembly 300 is positioned within the body of a patient, for example under a patient's mid-urethra, a medical operator can cut through the spacer 302 as described above and thus, cut through the intermediate portion 316 of the sleeve wall 310, without risking accidentally cutting the sling 304. As in the case of the embodiment of FIGS. 1 and 2, with the sleeve 306 so cut, the sleeve ends 320 and 322 may be pulled to remove the sleeve 306 from the patient's body, while leaving the sling 304 in place. The spacer 302 may be removed, for example, via the patient's vagina.

Figure 4A:
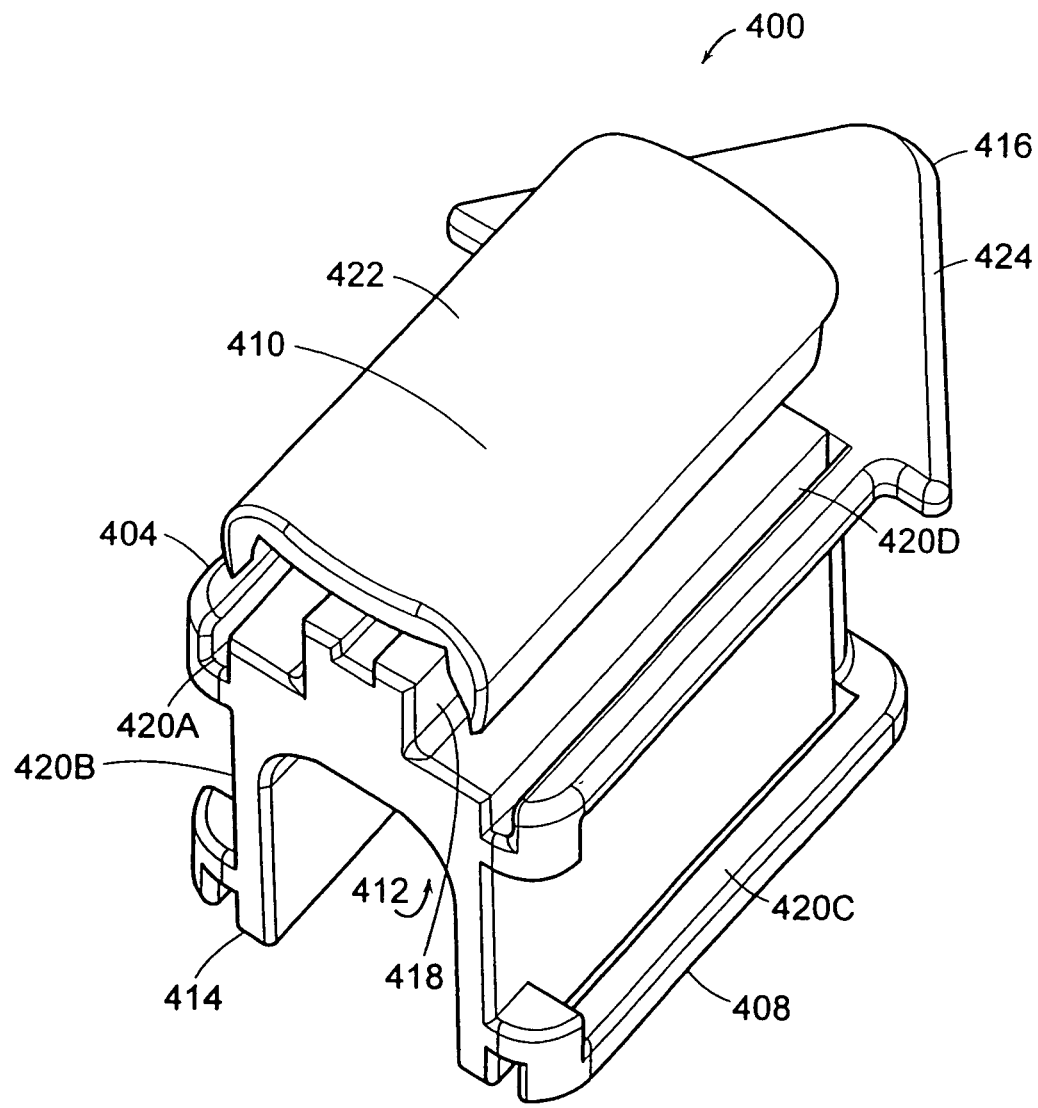
FIG. 4A depicts a perspective top view of a spacer according to another illustrative embodiment of the invention.
Figure 4B:
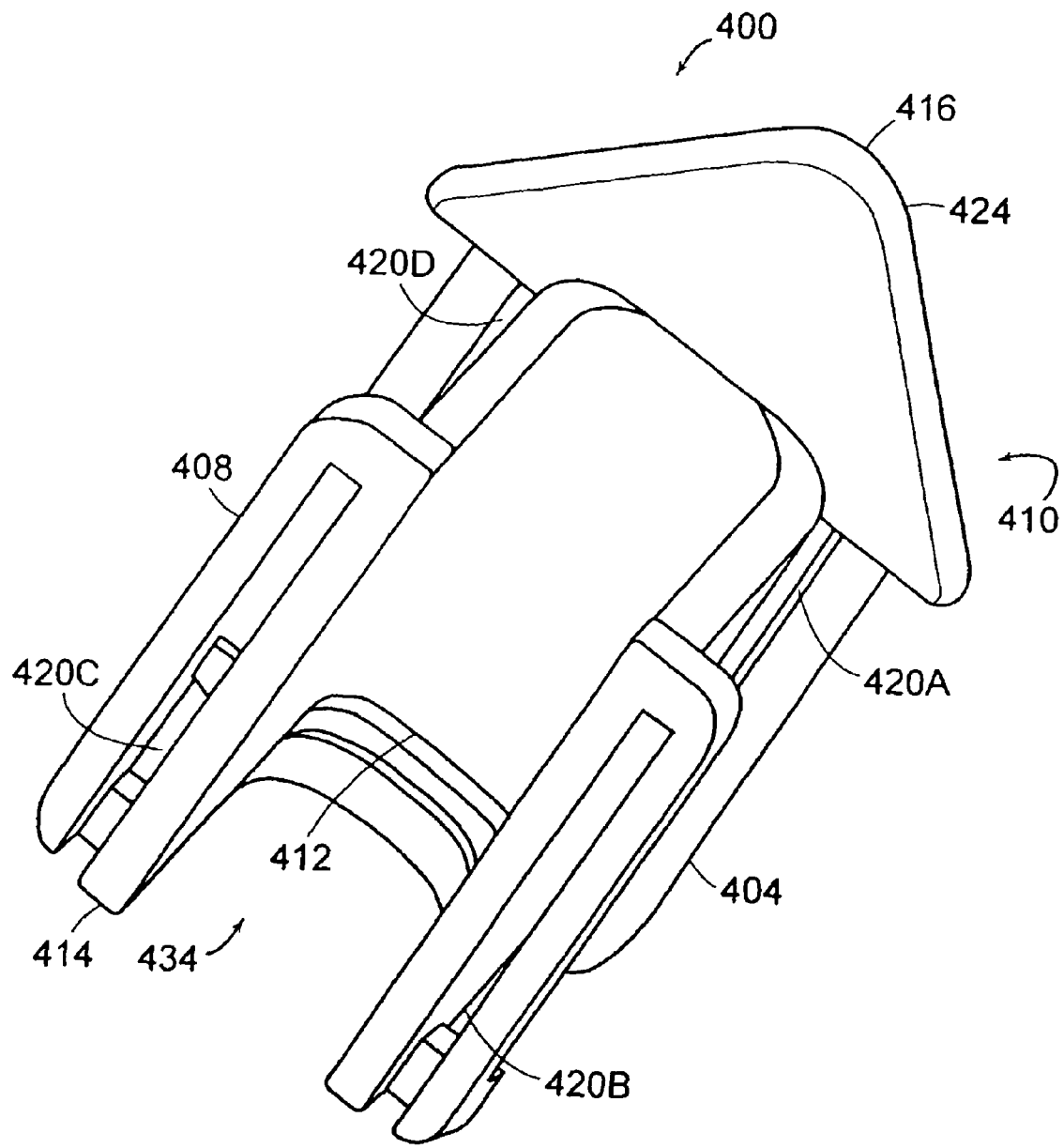
FIG. 4B depicts a perspective bottom view of the spacer of FIG. 4A.
Figure 4C:
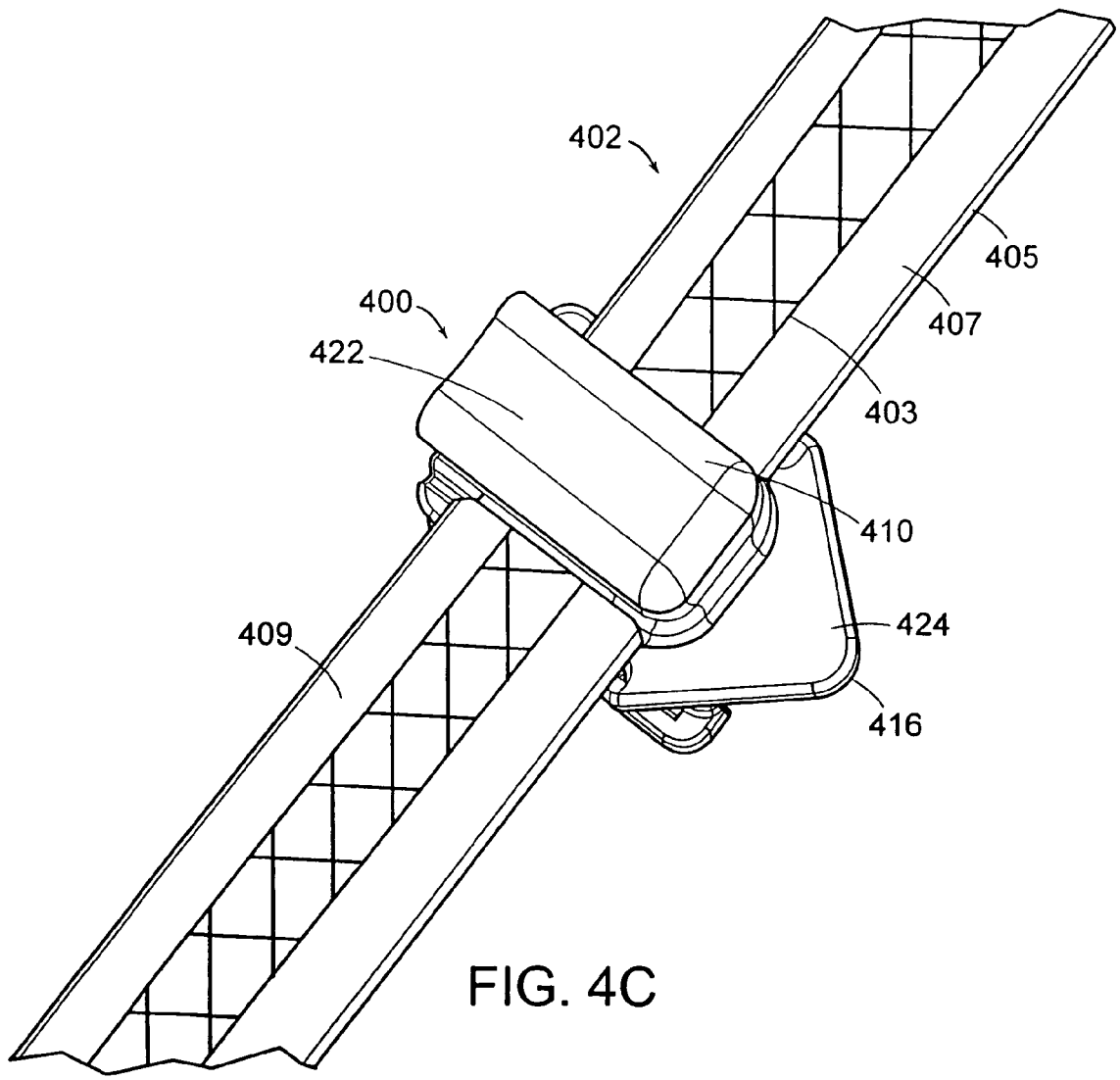
FIG. 4C depicts a perspective top view of the spacer of FIG. 4A employed with an exemplary sling assembly section according to an illustrative embodiment of the invention.
Figure 4D:
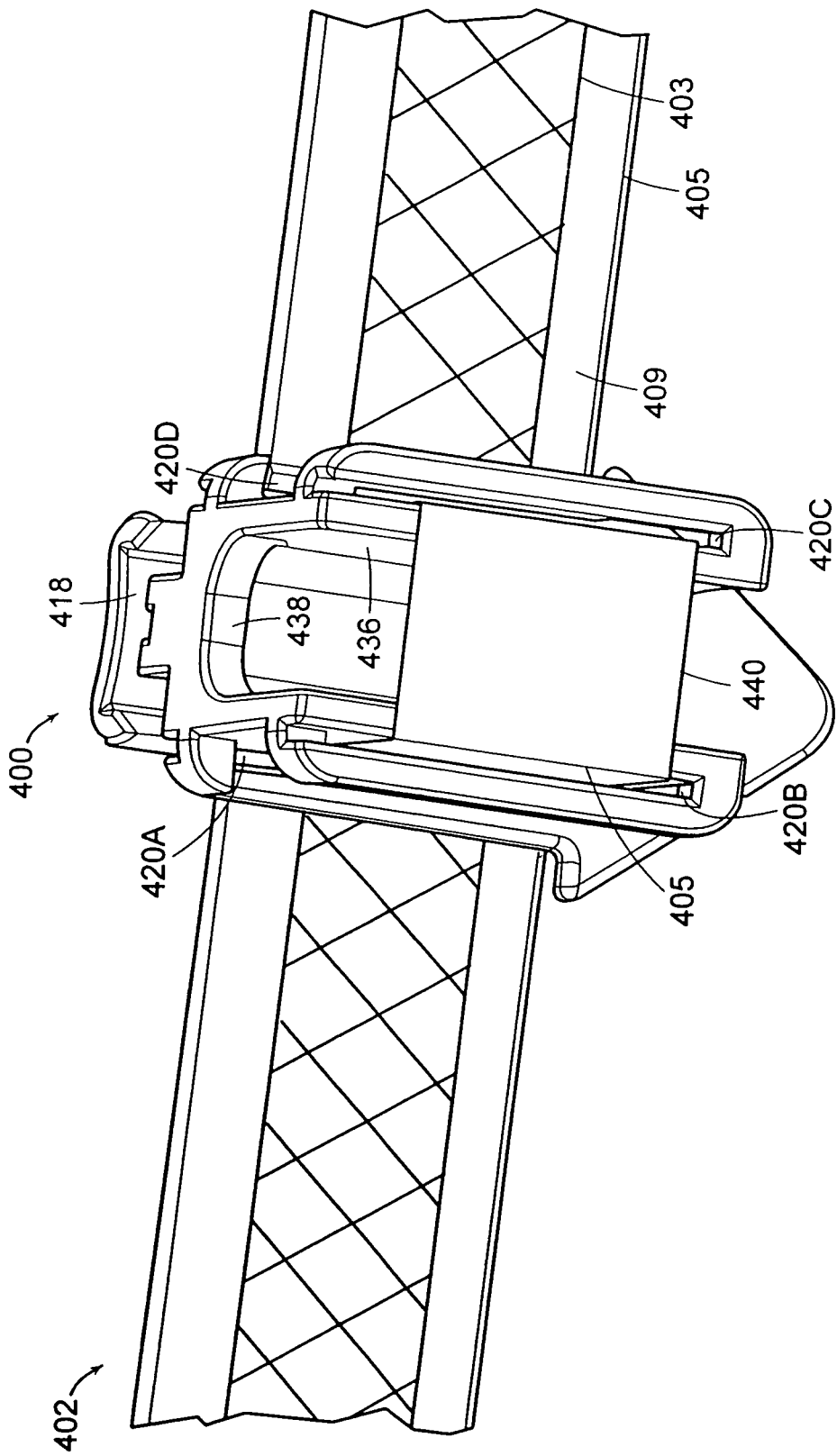
FIG. 4D depicts a perspective bottom view of the illustrative spacer and sling assembly section of FIG. 4C.
Figure 4E:
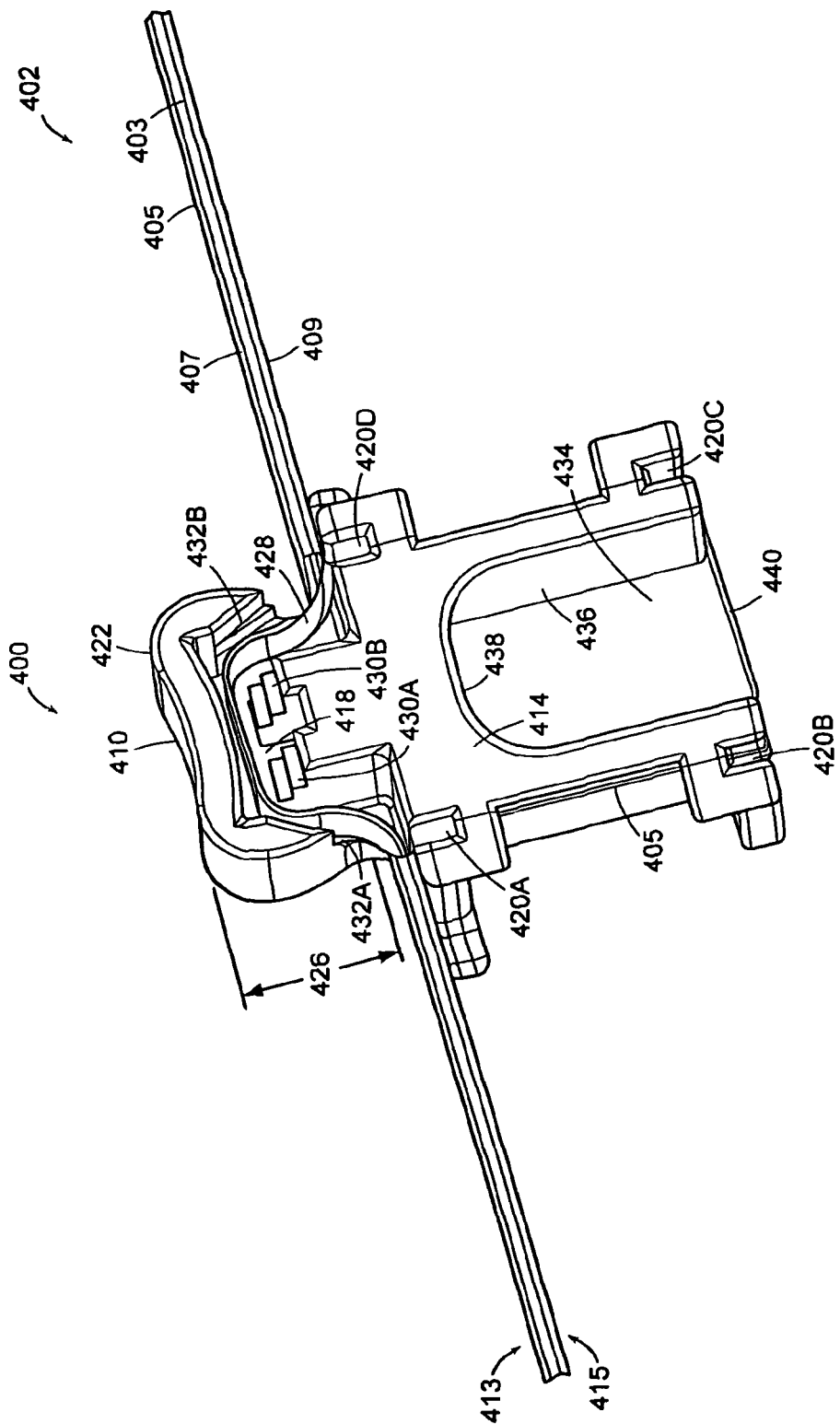
FIG. 4E depicts a perspective side view of the illustrative spacer and sling assembly section of FIG. 4C.

FIG. 4A depicts a perspective top view of a spacer 400 according to another illustrative embodiment of the invention, and FIG. 4B depicts a perspective bottom view of the spacer 400 of FIG. 4A. FIGS. 4C-4E depict various views of the spacer 400 employed with an exemplary sling assembly 402. Referring to FIGS. 4A4D, the spacer 400 includes a first side 404; a second side 408; a top side 410; a bottom side 412; a front side 414; and a back side 416 (i.e., a side that is closest to an operator of a delivery system). The spacer 400 also includes a sling engaging member, 418, formed as a sling slot positioned underneath the top side 410, and a sleeve engaging member 420, formed as two sleeve slots 420A and 420B positioned on the first side 404 of the spacer 400, and two sleeve slots 420C and 420D positioned on the second side 408 of the spacer 400. Alternatively, the spacer 400 may include any number of sides with any number of sling engaging members 418 or sleeve engaging members 420 positioned on any side.

The illustrative spacer 400 is constructed of a rigid medical grade plastic material or, alternatively, of other suitable rigid materials. However, in alternative embodiments, the spacer 400 may be formed from more flexible suitable materials. The top side 410 of the spacer 400 can serve as a tissue spacing member 422 for spacing the sling 403 of the sling assembly 402 away from the patient's tissue.

The illustrative spacer 400 also includes an indicator 424, which indicates the direction in which the spacer 400 should be removed following implantation of the mesh sling 403 at an anatomical site in the patient's body. The indicator 424, optionally, includes or is sized big enough to be used as a handle. Such a handle may be located on any of the sides of the spacer 400.

Referring particularly to FIGS. 4C-4E, the spacer 400 is depicted in various views employed with the sling assembly section 402. As in the case of previously described embodiments, the sling assembly 402 includes a mesh sling 403 partially enclosed by a sleeve 405. As in the case of the sleeves 106, 206 and 306, the sleeve 405 may be any suitable sleeve. Illustratively, it is shown as having a first sleeve wall 407 and a second sleeve wall 409, with the mesh sling 403 located between the first 407 and second 409 sleeve walls. Preferably, the first sleeve wall includes a discontinuity forming a gap exposing an intermediate portion of the mesh sling 403.

As depicted, the spacer 400 includes a tissue spacing member 422 at its top side 410. The height 426 of the tissue spacing member 422 may be varied to suit a particular clinical application. When the top side 410 of the spacer 400 is placed under a patient's urethra, as explained below with respect to FIGS. 5A and 5B, the height 426 of the tissue spacing member 422 governs the distance between an intermediate portion 428 of the mesh sling 403 and the patient's tissue, for example, the periurethral tissue. The tissue spacing member 422 can be any shape, for example, convex or concave, such that the spacer 400 easily fits under a patient's urethra, as explained below.

As shown in FIG. 4E, the sling engaging member 416 of the illustrative spacer 400 includes both step teeth 430A and 430B and spiral teeth 432A and 432B, which function as anchoring mechanisms for engaging the intermediate portion 428 of the mesh sling 403 when the mesh sling 403 is tensioned. When no tension is applied to the mesh sling 403 (i.e., when the operator has not yet begun to cut and remove the sleeve 405 from the patient's body), the mesh sling 403 sits loosely in the sling engaging member 418, without engagement by either the step teeth 430A and 430B or the spiral teeth 432A and 432B. In one embodiment, both the step teeth 430A and 430B and the spiral teeth 432A and 432B are tapered toward the front side 414 of the spacer 400. When the medical operator is ready to remove the spacer 400 from the sling assembly 402, the taper of the step teeth 430A and 430B and the spiral teeth 432A and 432B facilitate the process.

The illustrative spacer 400 also includes a receptacle 434 having an inner wall 436, which forms, for example, an archway 438, which is substantially U-shaped. Alternatively, the receptacle 434 may form any other suitable geometrical shape, including, but not limited to, an angular (e.g., an open ended polygon, such as a rectangle or triangle) or curved (e.g. substantially semicircular) shape. As depicted, the second sleeve wall 409, or alternatively, both the first sleeve wall 407 and the second sleeve wall 409, thread through the sleeve engaging members 420A-420D. The sleeve 403 forms a sleeve bridge 440 at the base of the archway 434, between the sleeve slots 420B and 420C. In other words, the spacer 400 distances the sleeve bridge 440 away from the mesh sling 403, thereby enabling a medical operator to cut the sleeve bridge 440 ut, without inadvertently also cutting the mesh sling 403.

Figure 5:
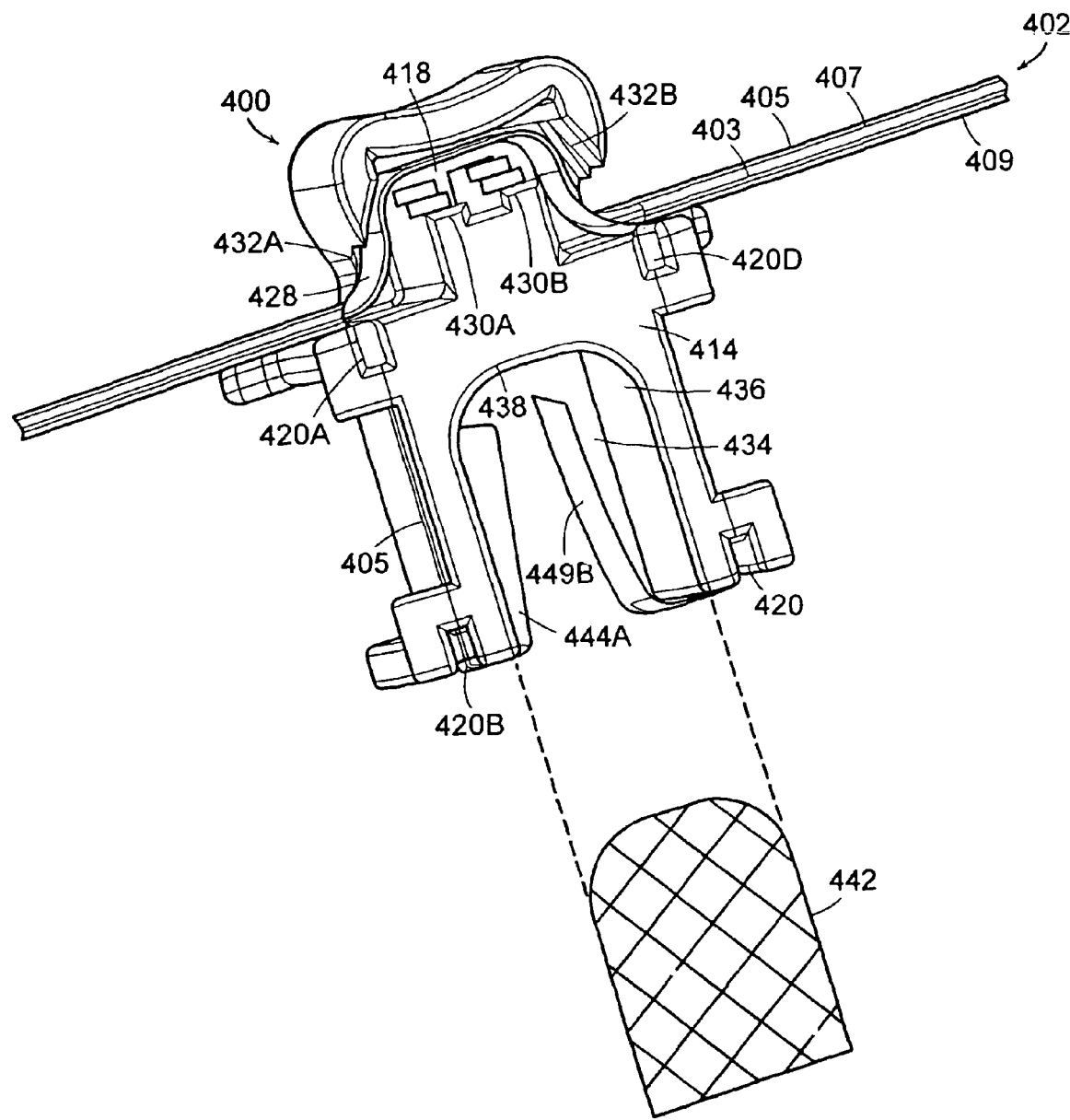
FIG. 5 depicts a perspective side view of the spacer and sling assembly section of FIGS. 4C-4E employing according to another illustrative embodiment of the invention.

FIG. 5 depicts a perspective side view of the spacer 400 and sling assembly section 402 of FIGS. 4C-4E employing an insert 442 according to another illustrative embodiment of the invention. The insert 442, for example, a plug, for mating within the receptacle 434 and holding a portion of the sleeve 405 in place within the receptacle 434. The spacer 400 and the sling assembly 402 can be preassembled before its placement in the patient's body. Once the insert 442 is removed, the sleeve bridge 440 may be cut thereby creating sleeve parts 444A and 444B, without risk of the mesh sling 403 also being inadvertently cut. Alternatively, prior to insertion of the sling assembly in the patient, the sleeve 405 can be cut to form the sleeve parts 444A and 444B. The plug 442 is then placed within the receptacle 434 to hold the sleeve parts 444A and 444B in place against the inner wall 436. So assembled, the sling assembly 402 and spacer 400 can then be delivered to the medical operator. Because the medical operator only has to remove the plug 442 from within the receptacle 434 of the spacer 400, and no sleeve cutting is required during sling delivery, the risk of damaging the sling 403, for example, from inadvertent cutting, during placement is reduced.

Figure 6A:
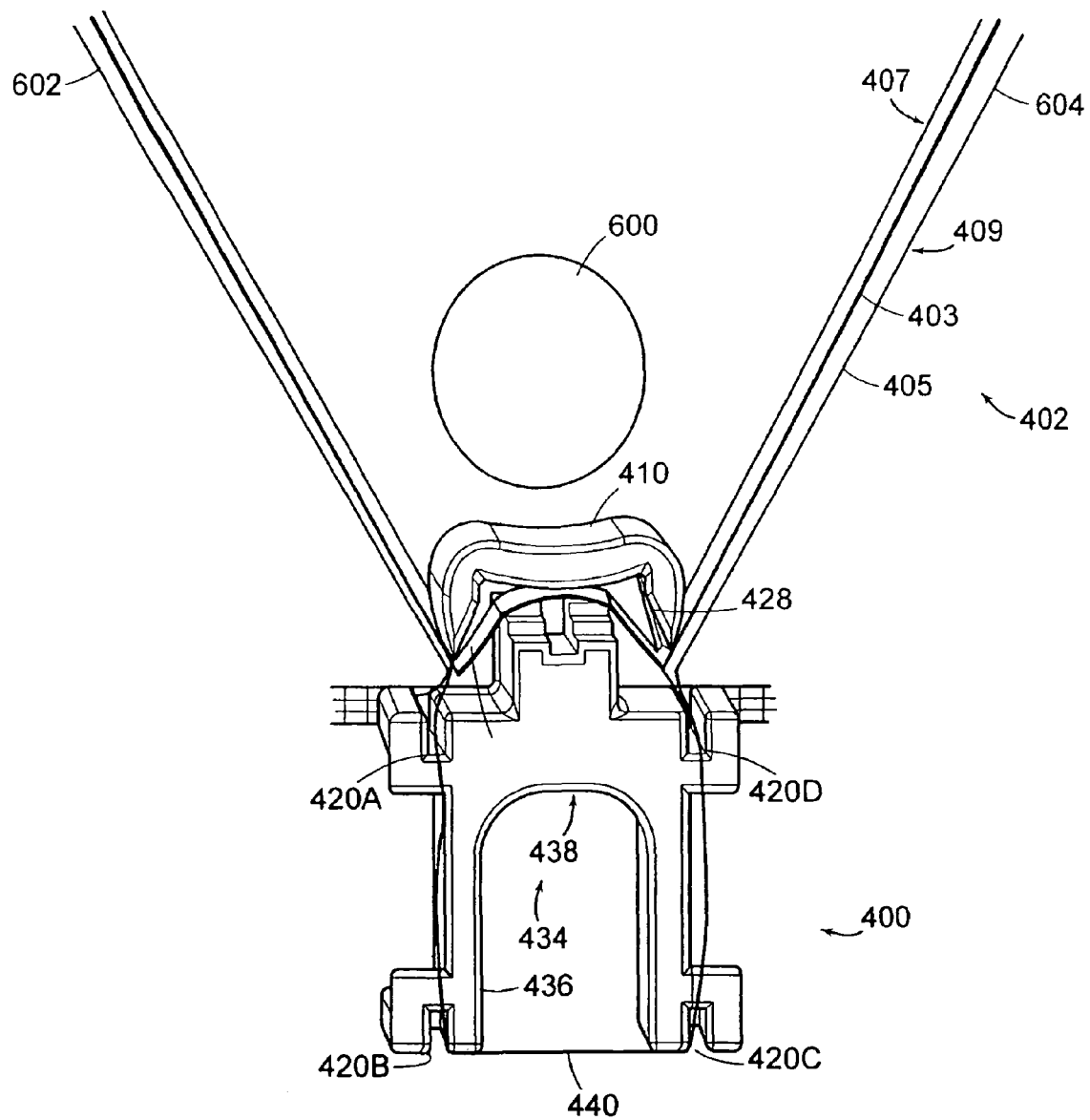
FIG. 6A depicts a perspective side view of the spacer and sling assembly section of FIG. 4C, positioned adjacent the urethra of a patient.

FIG. 6A depicts a perspective side view of the spacer 400 and sling assembly section 402 of FIG. 4C, positioned adjacent the urethra 600 of a patient, and FIG. 6B depicts a perspective side view of the illustrative spacer 400 and sling assembly section 402 of FIG. 6A after the sleeve bridge is cut, for example, subsequent to remove of the insert 442. The removal of the insert 442 and cutting of the sleeve 405 causes the sleeve parts 444A and 444B to hang free in the archway 434. Alternatively, the physician may leave the plug 442 in place and cut the sleeve 405 at a point, for example, between the sleeve slots 420A and 420B, thereby creating the sleeve part 444A, and at a point between the sleeve slots 420C and 420D, thereby creating the sleeve part 444B. As in the case of the embodiments of FIGS. 1-3B, by grasping the sleeve ends 602 and 604 and pulling, the medical operator can then remove the sleeve 405 from the patient's body, for example, through a surgical site at the abdominal wall, leaving the mesh sling 403 and the spacer 400 in place in the patient's body. The spacer 400 can then be removed, for example, via the patient's vagina.

Referring also to FIGS. 4A and 4B, during the removal of the sleeve 405 from the patient's body, the friction between the sleeve 405 and the mesh sling 403 causes the mid-length portion 428 of the mesh sling 403 to tension against step teeth 430A and 430B and spiral teeth 432A and 432B. As such, the spacer 400 prevents the mid-length portion 428 of the mesh sling 403 from moving beyond the mesh slot 418 during the sleeve 405 removal process. In other words, the mid-length portion 428 of the mesh sling 403 remains, throughout the sleeve removal process, in the mesh slot 418, under the top side 410 of the spacer 400, and, consequently, directly below the patient's urethra 600.

Figure 7A:
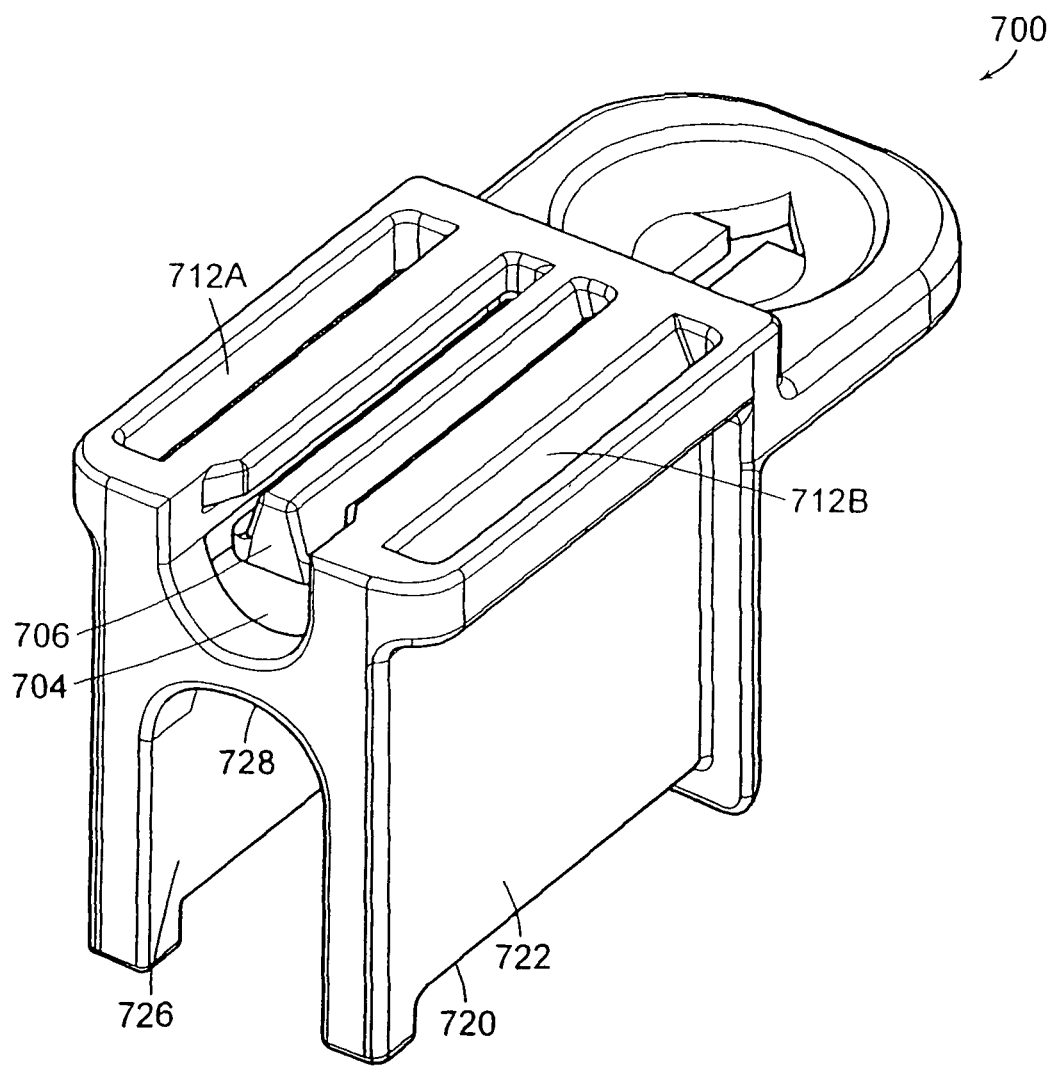
FIG. 7A depicts a perspective top view of a spacer according to another illustrative embodiment of the invention.
Figure 7B:
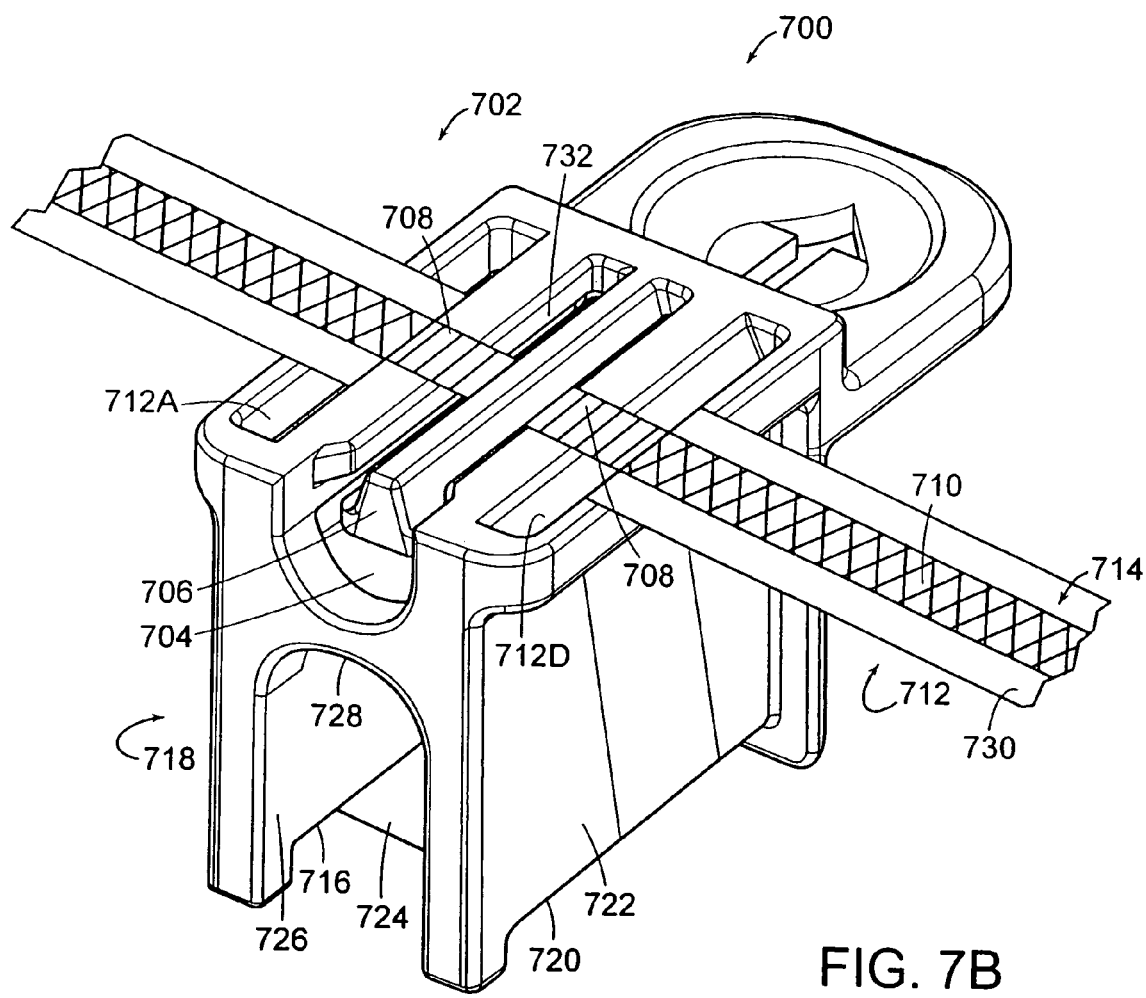
FIG. 7B depicts a perspective top view of the illustrative spacer of FIG. 7A employed with an exemplary sling assembly section according to an illustrative embodiment of the invention.

FIG. 7A depicts a perspective top view of a spacer 700 according to another illustrative embodiment of the invention, and FIG. 78 depicts a perspective top view of the illustrative spacer 700 of FIG. 7A employed with an exemplary sling assembly section 702. Referring to FIGS. 7A and 7B, the illustrative spacer 700 includes a sling engaging member 704 having a cantilever beam 706 as an anchoring mechanism. In the depicted embodiment, the cantilever beam 706 has an inverted T-shape. Alternatively, the cantilever beam 706 may assume other shapes. The cantilever beam 706, in a similar fashion to the step teeth 430A an 430B and the spiral teeth 432A and 432B of the spacer of FIGS. 4A-6B, engages a mid-length portion 708 of a mesh sling 710 when the mesh sling 710 is tensioned. The spacer 700 also includes sleeve engaging members 712A and 712B, which function substantially like the sleeve engaging members 420A and 420D, respectively, of the spacer 400 of FIG. 4.

Referring particularly to FIG. 7B, the second sleeve wall 712, or, alternatively, both the first sleeve wall 714 and the second sleeve wall 712, loop under a base 716 of the first side 718 of the spacer 700 and under a base 720 of the second side 722 of the spacer 700, rather than through sleeve engaging members, such as the sling engaging members 432B and 432c of the spacer 400 of FIG. 4, to form a sleeve bridge 724. In an alternative embodiment, the second sleeve wall 712, or, alternatively, both the first sleeve wall 714 and the second sleeve wall 712, may be disconnected at a point between the base 716 and the base 720 and held in place against the inner wall 726 of the archway 728 by a plug, such as the plug 442 of FIG. 5. As illustrated, the intermediate portion 708 of the mesh sling 710 is placed in the sling engaging member 704 and loops under the cantilever beam 706.

In operation, as the sleeve 730 is pulled off the mesh sling 710, intermediate portion 708 of the mesh sling 710 tensions and deflects the cantilever beam 706 into an opposing face (e.g., a face 732), thereby pinning the intermediate portion 708 of the mesh sling 710 between the cantilever beam 706 and the face 732. Following removal of the sleeve 730 from the patient's body, the cantilever beam 706 relaxes, thereby allowing for the removal of the intermediate portion 708 of the mesh sling 710 from the mesh slot 704.

Figure 8A:
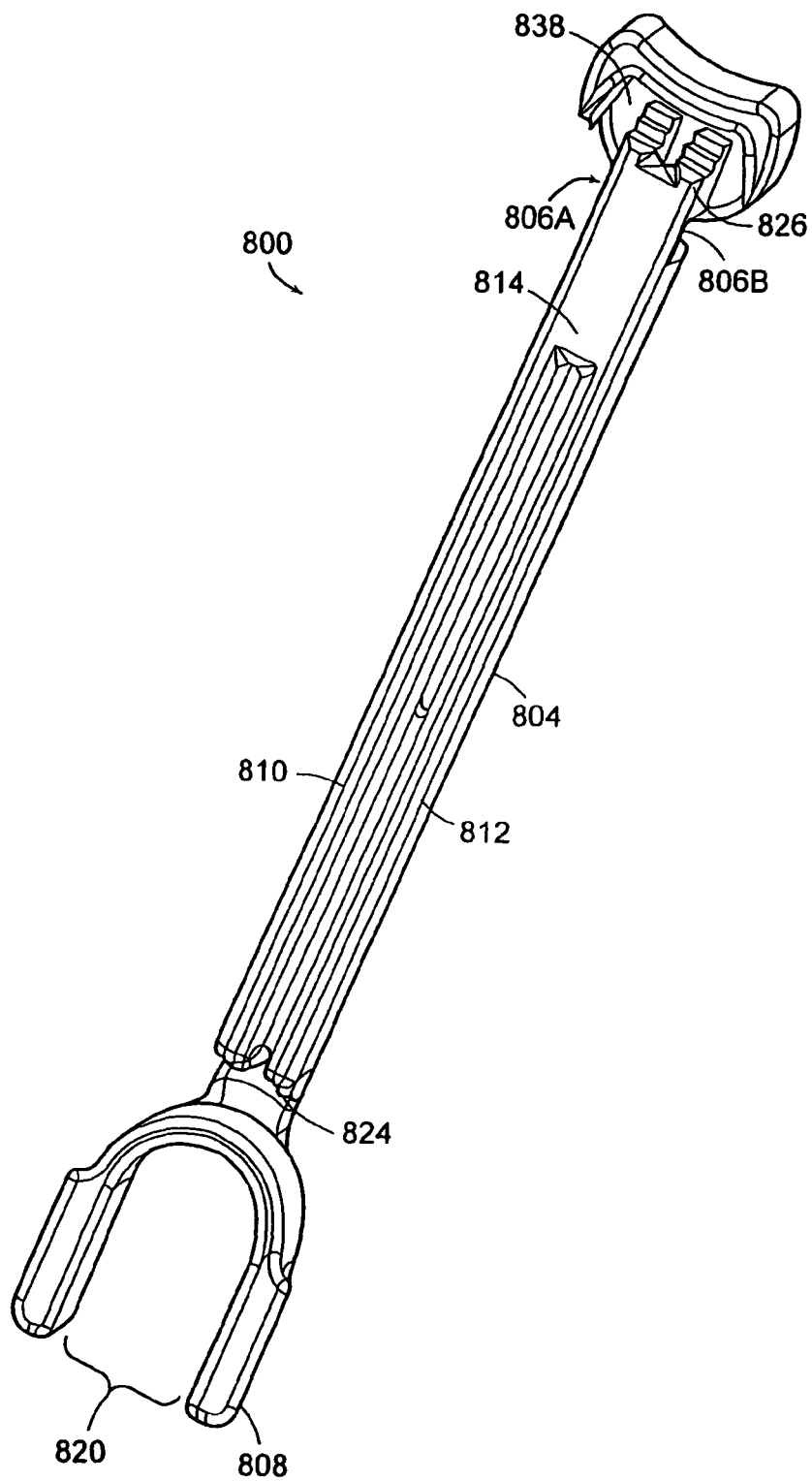
FIG. 8A depicts a perspective front view of a spacer according to another illustrative embodiment of the invention.
Figure 8B:
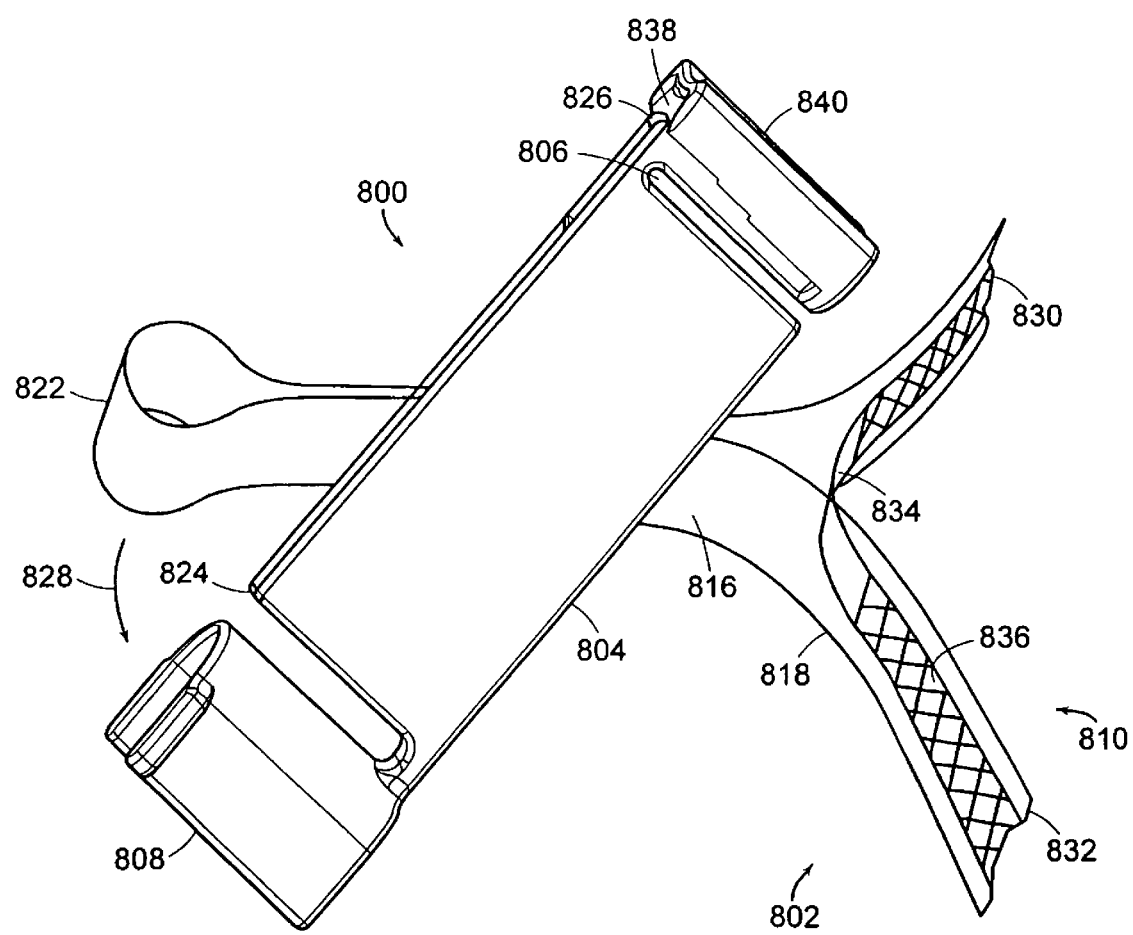
FIG. 8B depicts a perspective side view of the illustrative spacer of FIG. 8A employed with an exemplary sling assembly section according to an illustrative embodiment of the invention.

FIG. 8A depicts a perspective front view of a spacer 800 according to another illustrative embodiment of the invention, and FIG. 8B depicts a perspective side view of the spacer 800 of FIG. 8A employed with an exemplary sling assembly section 802. The spacer 800 includes an elongated shaft member 804 extending between a sling engaging member 806 and a sleeve engaging member 808. The elongated shaft member 804 has a proximal end 824 and a distal end 826 and includes two walls 810 and 812 extending along its length and forming a channel 814 from the proximal end 824 to the distal end 826 for traversal by an intermediate portion 816 of the sleeve wall 818. In one embodiment, the sleeve engaging member 808 may be, for example, U-shaped for forming a sleeve bridge 822, such as the sleeve bridge 440 of FIG. 6A, across its terminal end 820 for facilitating cutting of the second sleeve wall 818 by a medical operator. Alternatively, the sleeve engaging member 808 may be any suitable shape such as, for example, V-shaped or rectangularly-shaped.

With the spacer 800 and the sling assembly 802 engaged, the intermediate portion 816 of the second sleeve wall 818, or, alternatively, both the first sleeve wall 817 and the second sleeve wall 818, thread through the channel 814 of the elongated shaft member 804 and loop over span 820 of the U-shaped sleeve engaging member 808 to form the sleeve bridge 822, as indicated by arrow 828. The sleeve ends 830 and 832 then thread through the sleeve slots 806A and 806B, respectively, and function similarly to the sleeve slots 712A and 712B of FIGS. 7A and 7B. In a similar fashion to operation of the mesh slot 704 of the spacer 700 of FIGS. 7A and 7B, the intermediate portion 834 of the mesh sling 836 threads through the mesh slot 838.

One advantage of the spacer 800 is that the elongated shaft member 804 presents the sleeve bridge 822 to the medical operator at a greater distance from the mesh sling 836 than do the previously described embodiments. This increased distance further simplifies the process of cutting the sleeve bridge 822, and further eases the process of removing the sleeve from the patient's body. Moreover, the elongated shaft member 804 makes the task of removing the spacer 800 from the patient's body easier, as the medical operator need not reach as far into the patient's body to grasp the spacer 800 and remove it.

Figure 9:
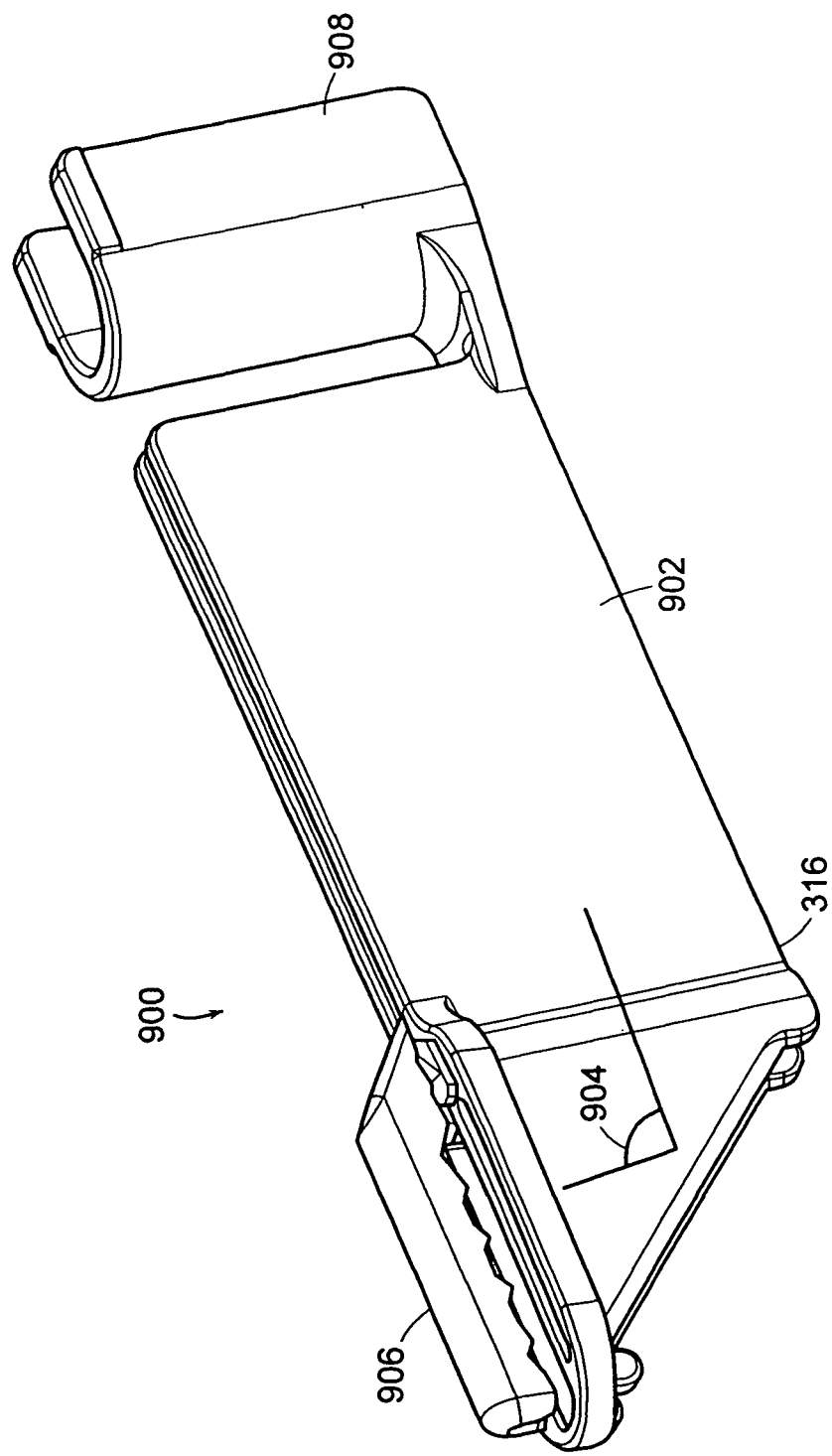
FIG. 9 depicts a perspective side view of a spacer according to another illustrative embodiment of the invention.

FIG. 9 is a perspective view of an spacer 900 having a similar configuration to the illustrative spacer 800 of FIGS. 8A and 8B, but including an elongated shaft member 902 bent at an angle 904, of up to about 90 degrees, relative to the top side 906 of the spacer 900. An advantage of this configuration is that positions the sleeve engaging member 908 to ease the procedure of cutting the sleeve bridge during removal of the sleeve from the patient's body.

Figure 10A:
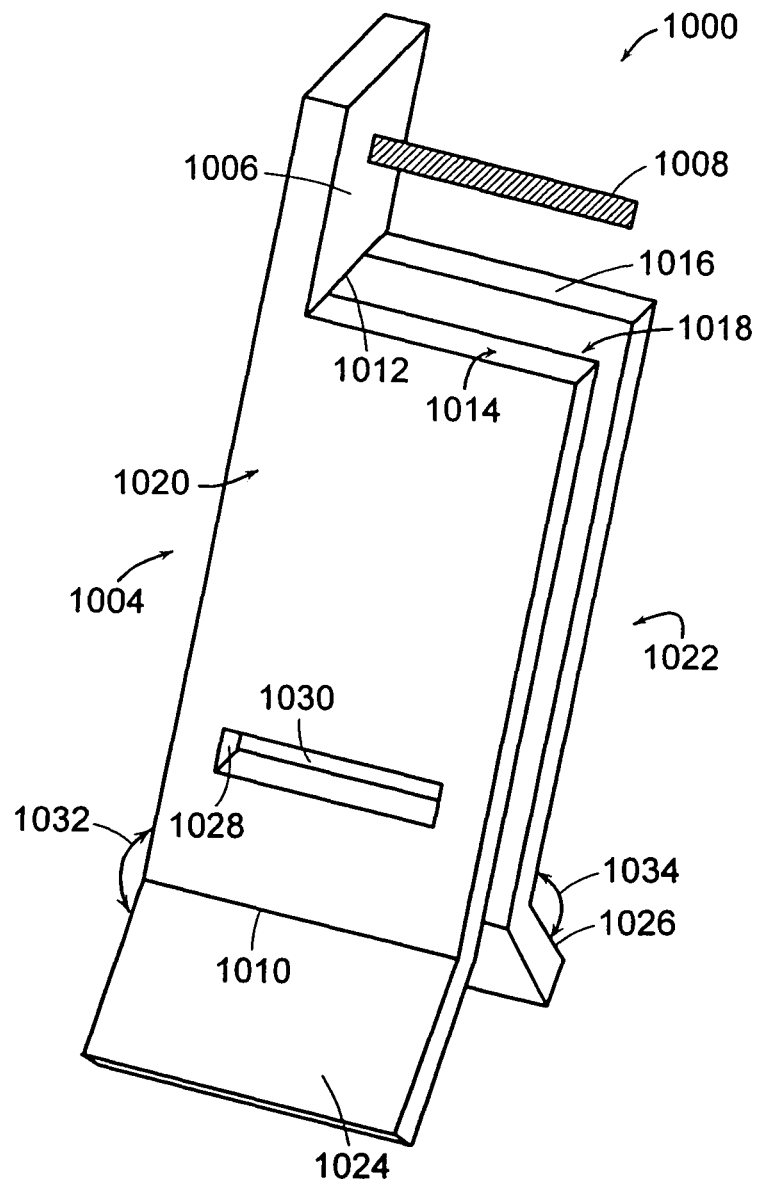
FIG. 10A depicts a perspective side view of a spacer according to another illustrative embodiment of the invention.
Figure 10B:
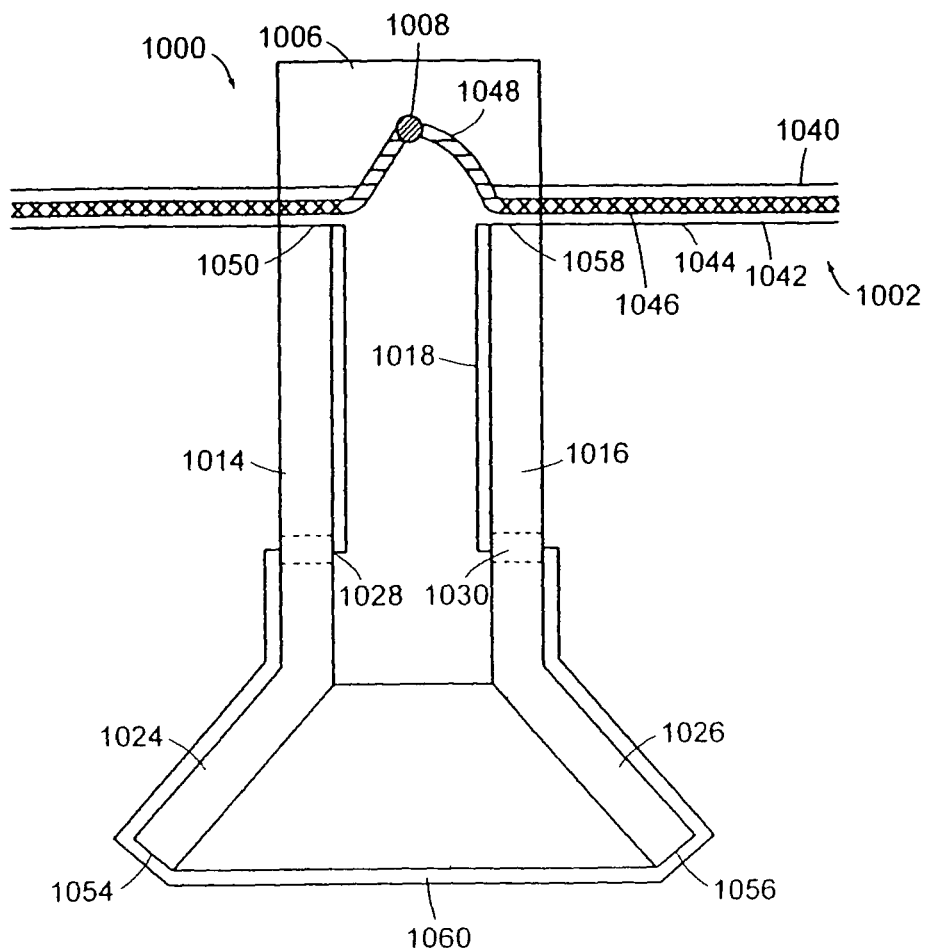
FIG. 10B depicts a plan view of the illustrative spacer of FIG. 10A employed with an exemplary sling assembly section according to an illustrative embodiment of the invention.

FIG. 10A depicts a perspective side view of a spacer 1000 according to another illustrative embodiment of the invention, and FIG. 10B depicts a plan view of the spacer 1000 of FIG. 10A employed with an exemplary sling assembly section 1002. As shown, the spacer 1000 includes a shaft 1004, an extension 1006, and a pin 1008 extending from the spacer 1000. The shaft 1004 includes a proximal end 1010, a distal end 1012, and first 1014 and second 1016 walls forming a channel 1018 extending from the proximal end 1010 to the distal end 1012. The first wall 1014 includes a first face 1020 and the second wall 1016 has a second face 1122. The spacer 1000 also includes first 1024 and second 1026 sleeve engaging members. As depicted, a first sleeve slot 1028 passes from the through the first 1014 and second 1016 walls across the channel 1018. The first sleeve engaging member 1024 extends at an angle 1032 from a base face 1020 of the wall 1014. Similarly, he second sleeve engaging member 1026 extends at an angle 1034 from the face 1022 of the second wall 1016. Preferably, the angles 1032 and 1034 are substantially equal. In some configurations, the angles 1042 and 1034 are both about 180 degrees. In another embodiment, the sleeve engaging members 1024 and 1026 are curved, rather than angled, with respect to the first 1014 and second 1016 walls. In another alternative embodiment, the sleeve engaging members 1024 and 1026 form a substantially V-shape. The extension 1006 extends distally from the distal end 1012 of the shaft 1004. The pin 1008 is fixed to and extends substantially orthogonally from the extension 1006.

Referring particularly to FIG. 10B, the second sleeve surface 1042, or, alternatively, both the first sleeve surface 1040 and the second sleeve surface 1042 thread across a top side 1040 of the first wall 1014, through the channel 1018, through the first sleeve slot 1028, across a base 1054 of the first sleeve engaging member 1024, across a base 1056 of the second sleeve engaging member 1026, through the second sleeve slot 1030, back through the channel 1018, and across a top side 1058 of the second wall 1016. In this way, the second sleeve wall 1042, or, alternatively, both first sleeve wall 1040 and the second sleeve wall 1042, form a sleeve bridge 1060 between the first sleeve engaging member 1024 and the second sleeve engaging member 1024. Preferably, the pin 1008 passes through the weave of an intermediate portion 1048 of the mesh sling 1046, so as to act as an anchoring mechanism that engages the intermediate portion 1048 of the mesh sling 1046. As such, the pin 1008 prevents movement of the intermediate portion 1046 of the mesh sling 1048 when the mesh sling 1048 is tensioned during removal of the sleeve 1044 from the patient's body.

Figure 11A:
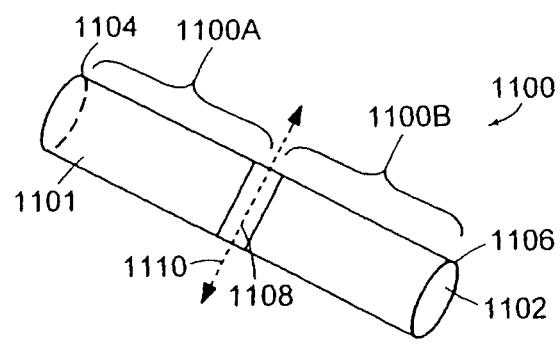
FIG. 11A depicts a perspective top view of a spacer according to another illustrative embodiment of the invention.

FIG. 11A depicts a perspective top view of a spacer 1100 according to another illustrative embodiment of the invention. The spacer 1100 is generally tubular in shape and includes a wall 1101 defining a lumen 1102 extending between first 1104 and second 1106 apertures. As depicted in FIG. 11A, the spacer 1100 includes a slot shaped aperture 1108 formed at an intermediate location in the tube wall 1101 between the first 1104 and second 1106 apertures. The aperture 1108 effectively divides the spacer 1100 along the center line 1110 into two substantially equal halves 1100a and 1100b.

Figure 11B:
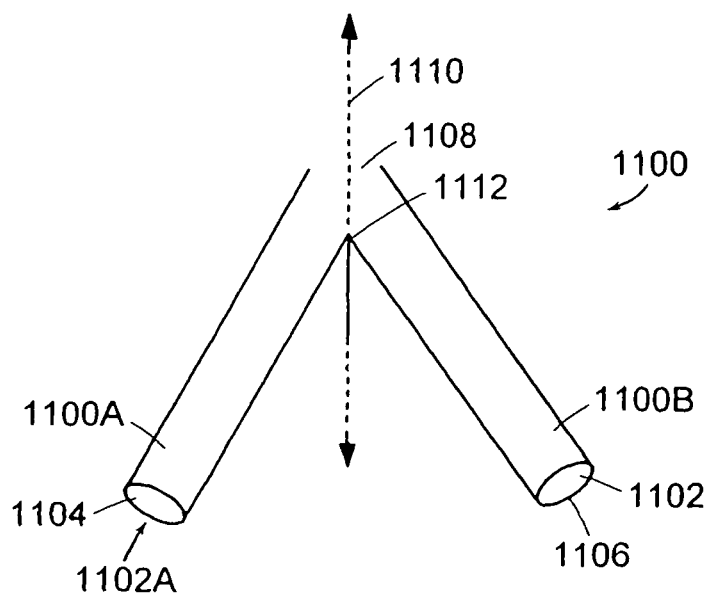
FIG. 11B depicts a perspective side view of the illustrative spacer of FIG. 11A, bent at its mid-point according to illustrative embodiment of the invention.

FIG. 11B depicts a perspective side view of the illustrative spacer 1100 of FIG. 11A, bent at its mid-line 1110 according to illustrative embodiment of the invention. So bent, the two spacer halves 1100a and 1100b are formed into a substantially V-shape, with a vertex at 1112 and one leg including a first lumen section 1102a and the other leg including the second lumen section 1102b. In an alternative illustrative embodiment, the first and second spacer halves 1100a and 1100b may form a substantially U-shaped or rectangularly-shaped spacer. In other illustrative embodiments, the tubular shape of the spacer 1100 may be flattened, with the aperture 1108 formed on one of the resulting sides. As in the case of the previously discussed spacer embodiments, the spacer 1100 may be made of a polymer or other suitable material.

Figure 11C:
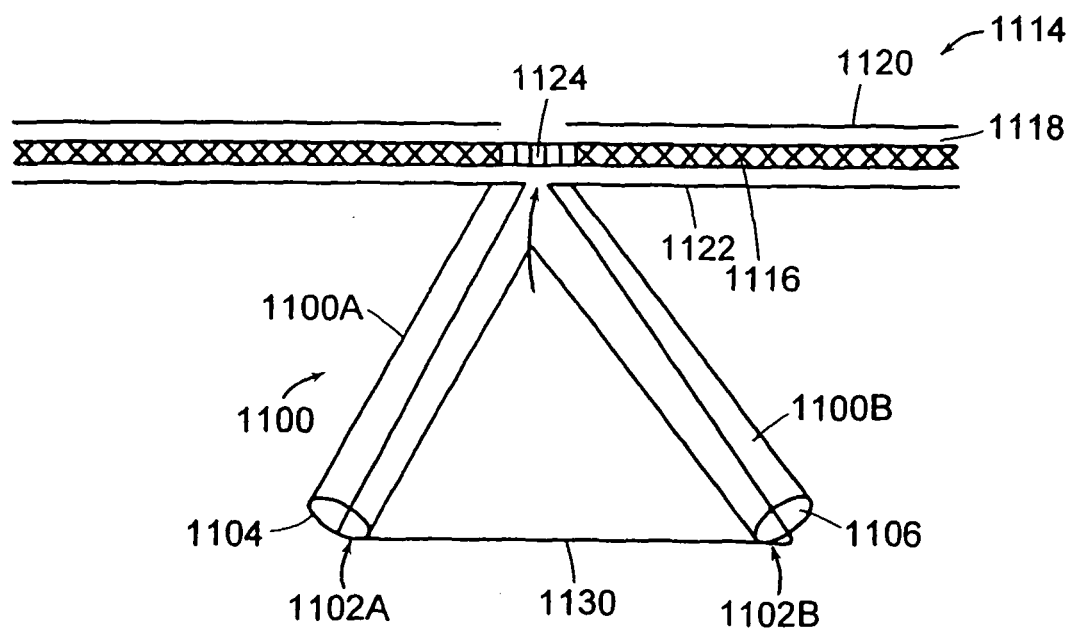
FIG. 11C depicts a perspective side view of the illustrative spacer of FIG. 10B employed with an exemplary sling assembly section according to an illustrative embodiment of the invention.

FIG. 11C depicts a perspective side view of the spacer 1100, bent in accord with the illustrative embodiment of FIG. 10B, employed with an exemplary sling assembly section 1114. The sling assembly 1114 includes a mesh sling 111, at least partially enclosed by a sleeve 1118. As depicted, the second sleeve surface 1122, or, alternatively, both the first sleeve surface 1120 and the second sleeve surface 1122, pass through the aperture 1108 at the vertex 1112. The second sleeve surface 1122 passes through the first lumen section 1102a, through the first aperture 1104, across and into the second aperture 1106, through the second lumen section 1102b and back out the aperture 1108 to form a sleeve bridge 1130 between the first aperture 1104 and the second aperture 1106.

Figure 11D:
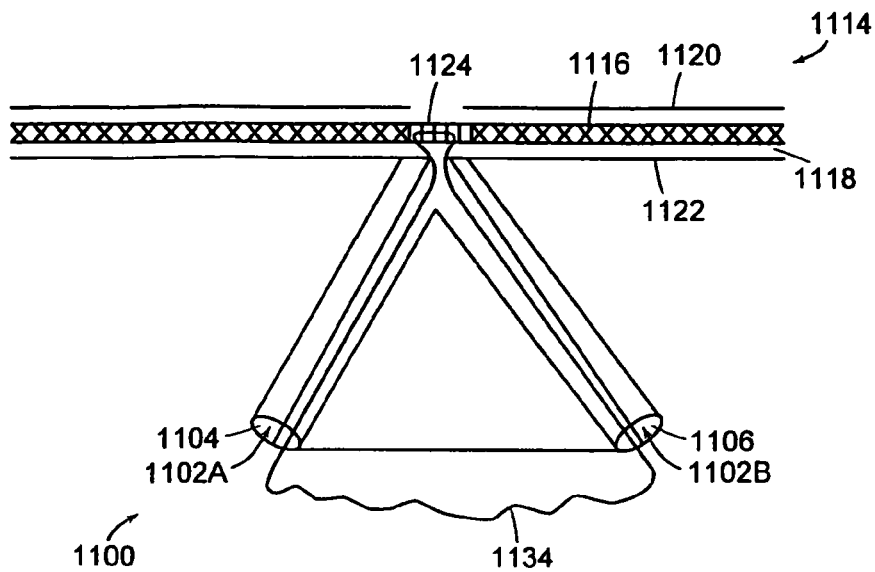
FIG. 11D depicts a perspective side view of an anchoring mechanism according to an illustrative embodiment of the invention employed with the illustrative spacer and sling assembly of FIG. 11C.

FIG. 11D depicts a perspective side view of the spacer 1100 and sling assembly 1114 configuration of FIG. 11C employing and anchoring mechanism according to an illustrative embodiment of the invention. In the embodiment of FIG. 11D, the anchoring mechanism includes a suture 1134 threaded through the weave of an intermediate portion 1124 of the mesh sling 1116, so as to engage the intermediate portion 1124. The suture 1134, in a similar fashion to the sleeve wall 1122, passes through the aperture 1108 and the first 1102a and second 1102b lumen sections, and forms a suture bridge 1134. As such, the suture 1132 prevents movement of the intermediate portion 1124 of the mesh sling 1116 when the mesh sling 1116 is tensioned during removal of the sleeve 1118 from the patient's body.

Figure 11E:
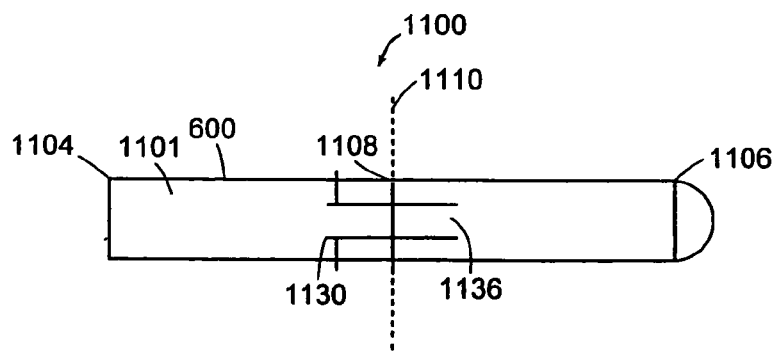
FIG. 11E depicts a bottom view of the spacer of FIG. 11A further formed to include a truss according to an illustrative embodiment of the invention.
Figure 11F:
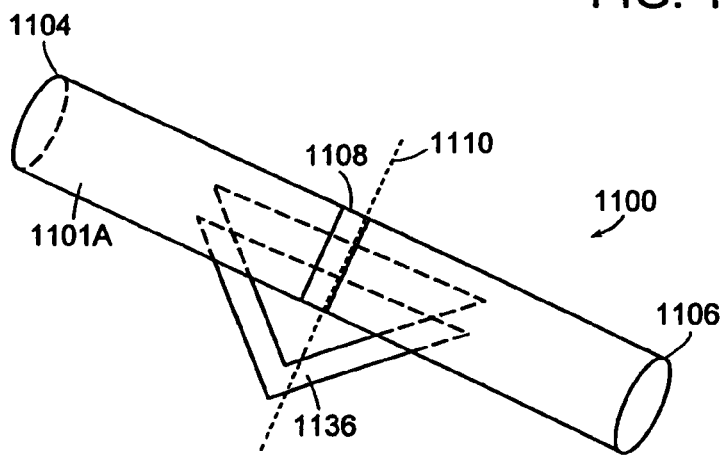
FIG. 11F depicts a perspective top view of the illustrative spacer of FIG. 10E.
Figure 11G:
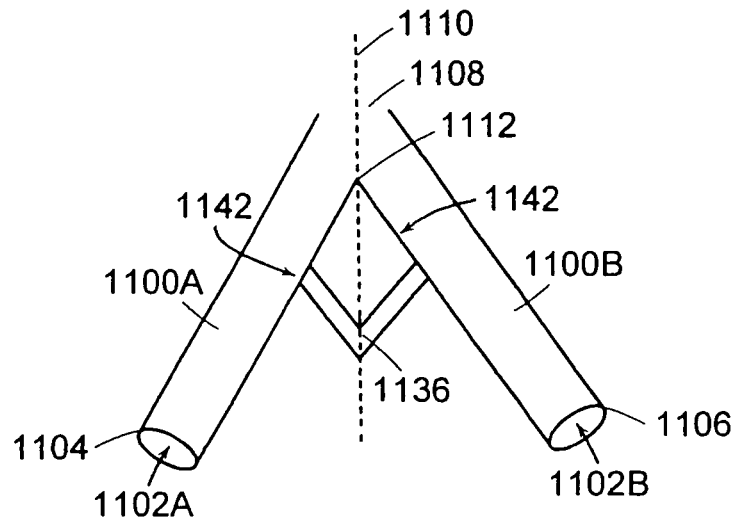
FIG. 11G depicts a perspective side view of the illustrative spacer of FIG. 10F, bent at its mid-point according to another illustrative embodiment of the invention.

FIG. 11E depicts a bottom view of the spacer 1100 further formed to include a truss 1136 according to an illustrative embodiment of the invention. FIG. 11F depicts a perspective top view of the spacer 1100 of FIG. 10E. FIG. 11G depicts a perspective side view of the spacer 1100 of FIG. 10E bent along its mid-line 1110, according to further illustrative embodiment of the invention. Referring to FIGS. 11E-11G, first 1138 and second 1140 substantially parallel slits are formed in the wall 1101 to form the truss 1136 to be substantially symmetrical about the center line 1110. The spacer 1100 may or may not be flattened during this process. As depicted in FIGS. 11F and 11G, the spacer 1100 is then folded into the V-shape of FIG. 11B, causing the truss 1136 to fold out of and away from the wall 1101, thereby creating a slot 1142, between slits 1138 and 1140.

Figure 11H:
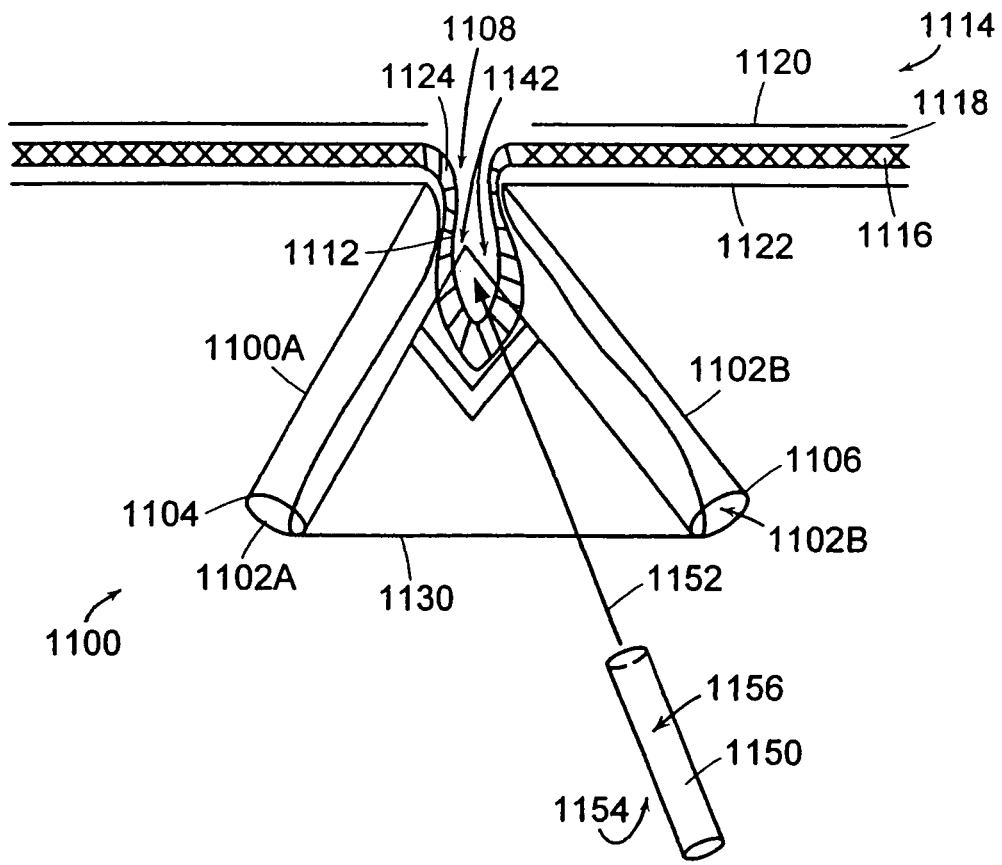
FIG. 11H depicts a perspective side view of the illustrative spacer of FIG. 10G employed with an exemplary sling assembly section according to an illustrative embodiment of the invention.

FIG. 11H depicts the spacer 1100 configured as depicted in FIG. G and employed with the exemplary sling assembly 1114. In the illustrative embodiment of FIG. 11H, the sleeve 1118 traverses the spacer 1100 to form the sleeve bridge 1130 in the same manner as described above with respect to the embodiment of FIG. 11C. Additionally, the intermediate portion 1124 of the sling 1116 passes through the slot-shaped aperture 1108 out the aperture 1142 in the first spacer half 1100a and rests on top of the truss 1136. An anchoring mechanism, for example, an anchor tube 1150, may be used to secure the intermediate mesh portion 1124 against the truss 1136. As indicated by arrow 1152, the anchor tube 1150 is placed between the intermediate sling portion 1124 and the wall 1101. In the illustrative embodiment, an lower portion 1154 of the outer of the anchor tube 1150 pins the intermediate sling portion 1124 against the truss 1136, while an upper portion 1156 of the outer surface of the anchor tube 1150 rests against the outer wall 1101 of the spacer 1100 near the vertex 1112. As such, the anchor tube 1150 prevents movement of the intermediate sling portion 1124 when the mesh sling 1116 is tensioned during removal of the sleeve 1118 from the patient's body.

The truss 1136, in this embodiment of the invention, also prevents the spacer halves 1101a and 1101b from moving towards one another when the sleeve 1116 is tensioned to place the spacer 1100 under the patient's urethra. Moreover, as illustrated, this embodiment of the invention allows for a greater amount of slack in the intermediate sling portion 1124.

Figure 12:
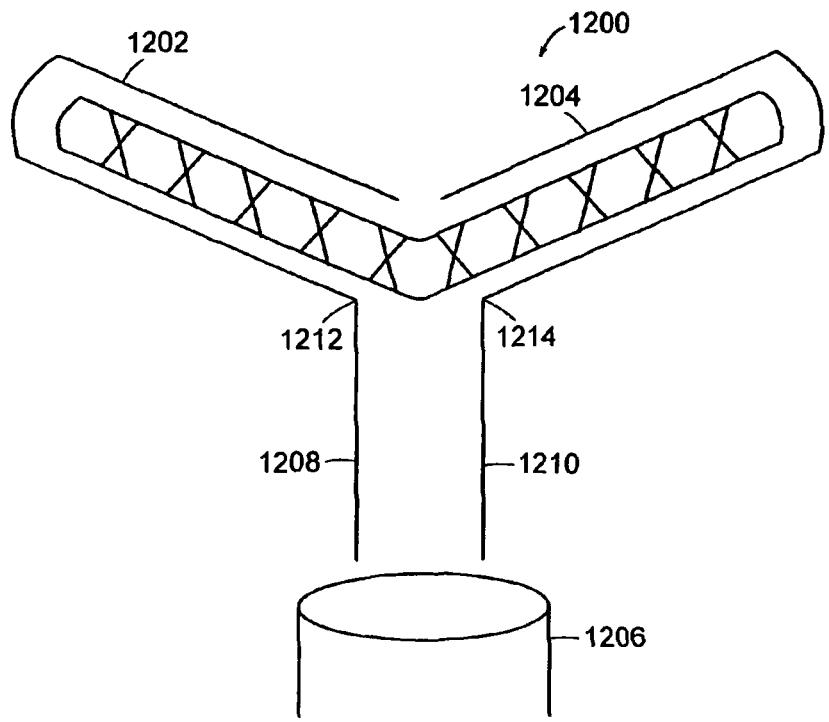
FIG. 12 depicts a perspective side view of a spacer and a sling assembly according to an illustrative embodiment of the invention.

FIG. 12 depicts the sling assembly 1200 including two sleeves 1202 and 1204 employed with a tubular spacer 1206 according to another illustrative embodiment of the invention. In this embodiment, the sleeve tails 1208 and 1210 extend from the proximal ends 1212 and 1214 of the sleeves 1202 and 1204, respectively, and fit into the tubular spacer 1206. In the illustrative embodiment, the tubular spacer 1206 is substantially cylindrical. Alternatively, the tubular spacer 1206 can be flattened. The tubular spacer 1206 can be formed from any suitable material, such as a rigid or tearable polymer material.

Figure 13:
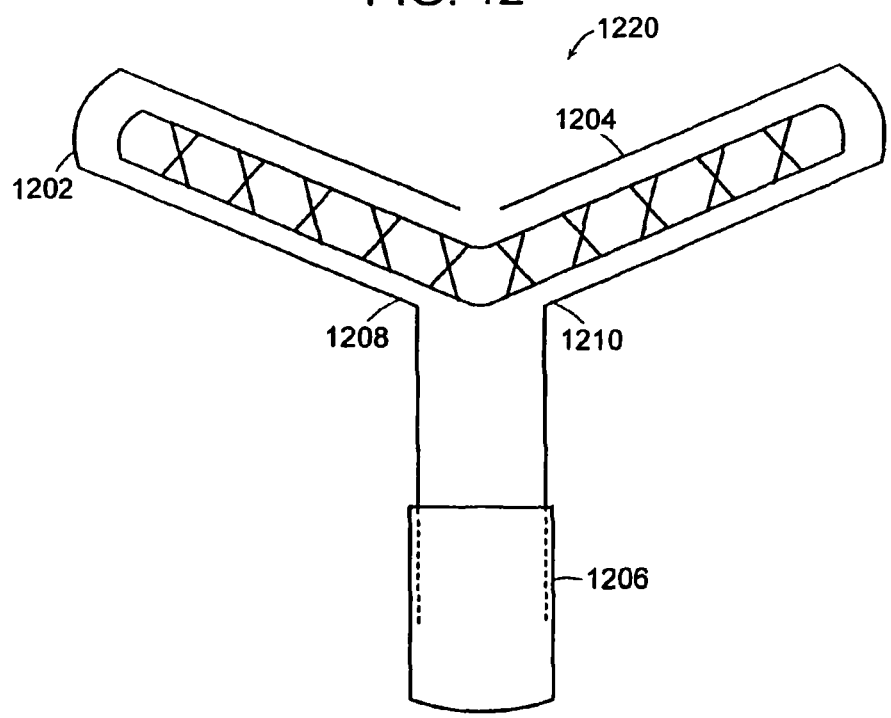
FIG. 13 depicts a perspective side view of the spacer and sling assembly of FIG. 12 where the sling ends are held in the spacer.

FIG. 13 depicts a further illustrative embodiment of the tubular spacer 1206, wherein the sleeve tails 1208 and 1210 are fixed to an inner surface 1216 of the tubular spacer 1206, for example, by gluing or heating.

Figure 14:
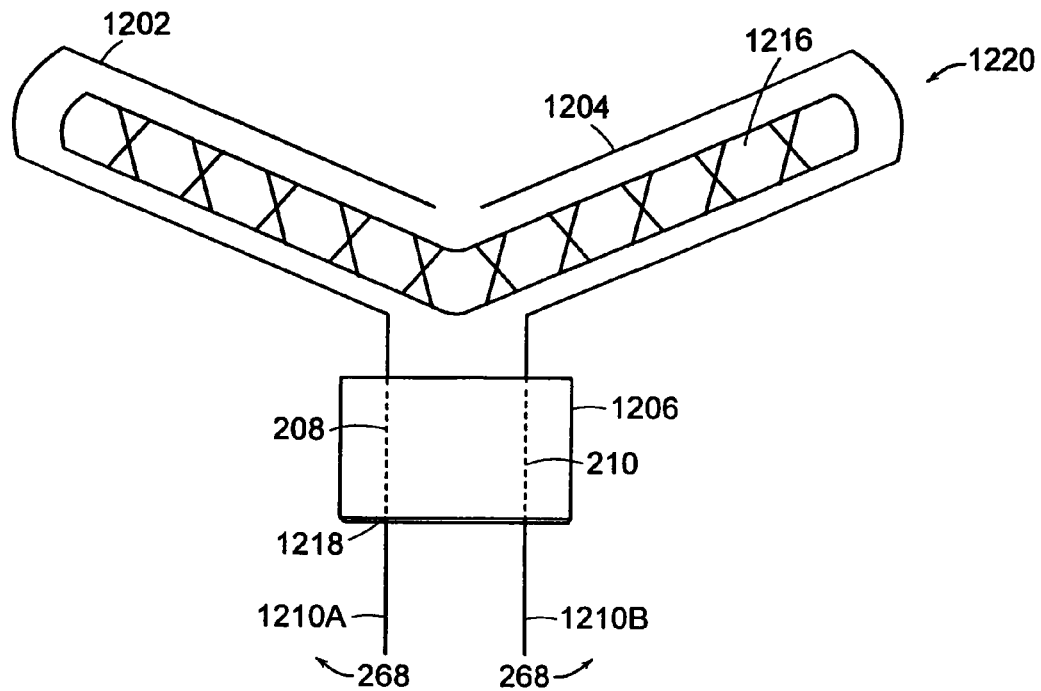
FIG. 14 depicts a perspective side view of the spacer and sling assembly of FIG. 12 according to a further illustrative embodiment of the invention.

FIG. 14 depicts another illustrative embodiment of the tubular spacer 1206, in which the spacer 1206 is formed from the same or a similar plastic materials as the sleeves 1202 and 1204, such as, for example, polyethylene. The sleeve tails 1210A and 1210B extend from the proximal end 1218 of the tubular spacer 1206. Once the sling assembly 1220 and the spacer 1206 are correctly positioned, the medical operator removes the sleeves 1020 and 1204 from about the sling 1216. In this embodiment, the sleeve tails 1210A and 1210B couple to the tubular spacer 1206 by, for example, heat sealing. The physician grasps the sleeve tails 1210A and 1210B and peels the sleeve tails 1210A and 1210B apart, as indicated by arrows 268.

Figure 15:
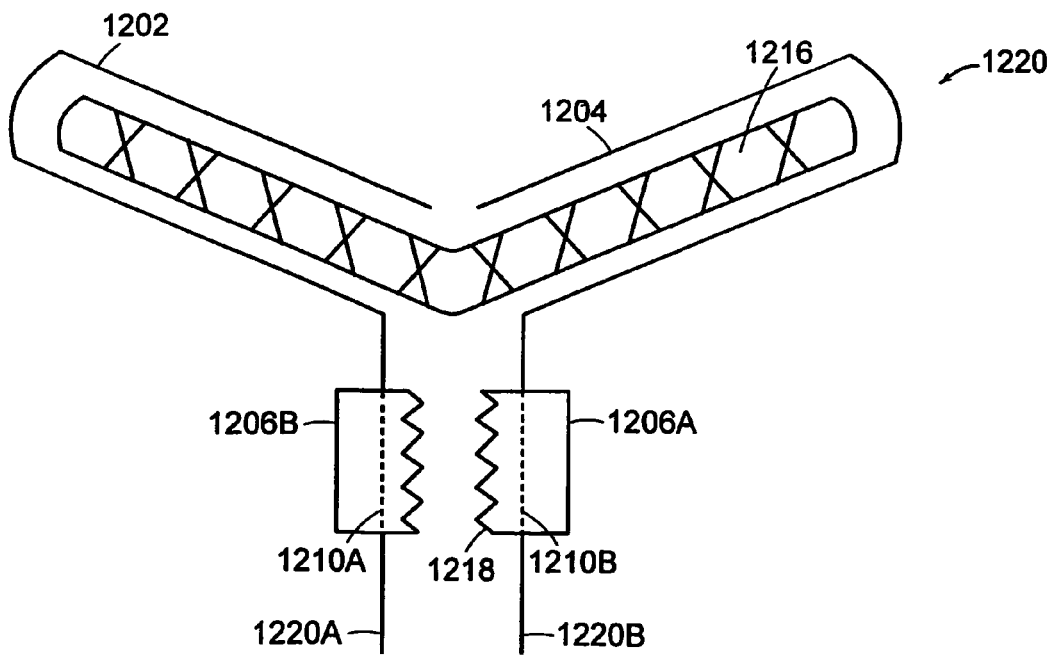
FIG. 15 depicts an approach to removing the spacer of FIG. 12 according to an illustrative embodiment of the invention.

As depicted in FIG. 15, in peeling apart the sleeve tails 1210A and 1210B, the soft plastic tubular spacer 1206 is separated into a portion 1206A and 1206B. By gasping the distal ends 1220A and 1220B of the sleeves ends 1210A and 1210B, the physician removes both portions of the now separated soft plastic tubular spacer 1206A and 1206B, and the sleeves 1202 and 1204 from the patient's body, leaving behind the sling 1216 in the patient's body.

Additionally, it should be noted that Applicants intend any operable embodiments existing between the systems, methods, devices, and applications thereof herein incorporated by reference and the illustrative embodiments described above to be considered within the scope of the inventions disclosed herein and, as such, claimable subject matter. The spacers as previously described may be made in various configurations and from various materials suited to the application in which they are used, so long as the spacer functions to create a space between the sling and the portion of the sleeve to be separated for removal, thereby decreasing the chance of damaging the sling during sleeve removal. Also, spacers of the invention can be colored so as to enhance visibility in the body and its location along the sleeve so as to provide a visual indicator of approximately the midpoint of the sling so as to facilitate proper placement of the sling in the body.

Variations, modifications, and other implementations of what is described herein will occur to those of ordinary skill without departing from the spirit and scope of the invention. Accordingly, the invention is not to be limited only to the preceding illustrative description.

What is claimed is:

1. A sling delivery system comprising;
an elongate sling;
a sleeve covering at least a portion of the sling; and
a spacer coupled to at least a portion of the sleeve, the spacer configured to position a portion of the sleeve away from the sling.

2. The system of claim 1, wherein the spacer positions a portion of the sleeve away from an intermediate portion of the sling.

3. The system of claim 1, wherein the sleeve comprises a first side and a second side and the spacer positions a portion of the second side of the sleeve away from the sling.

4. The system of claim 3, wherein the first side of the sleeve has a discontinuity.

5. The system of claim 4, wherein the discontinuity is located opposite the spacer.

6. The system of claim 1, wherein at least a portion of the spacer is located between the sling and the portion of the sleeve positioned away from the sling.

7. The system of claim 1, wherein the spacer at least partially encloses the portion of the sleeve positioned away from the sling.

8. The system of claim 7, wherein the spacer includes an indicator for identifying a portion of the spacer that includes a portion of the sleeve positioned away from the sling.

9. The system of claim 1, wherein a portion of the sleeve positioned away from the sling is affixed to the spacer.

10. The system of claim 9, wherein the sleeve is not affixed to any portion of the spacer other than an end of the spacer farthest from the sling.

11. The system of claim 1, wherein the spacer is a separate component from the sleeve.

12. A method for delivering a sling, the method comprising:
   delivering a sling assembly that comprises:
      a sling;
      a sleeve covering at least a portion of the sling; and
      a spacer for positioning a portion of the sleeve away from the sling; and
   cutting the spacer.

13. The method of claim 12, wherein the portion of the sleeve is positioned such that cutting the spacer also cuts the sleeve to form two sleeve ends.

14. The method of claim 13, further comprising:
   removing each of the two sleeve ends after cutting the spacer.

15. The method of claim 12, wherein:
   the sleeve comprises first and second sides;
   the spacer positions the second side of the sleeve away from the sling; and
   the first side of the sleeve comprises a discontinuity.

16. The method of claim 15, wherein cutting the spacer also cuts the second side of the sleeve.

17. The method of claim 12, wherein cutting the spacer comprises a single incision.

18. The method of claim 12, further comprising:
   removing the spacer after cutting the spacer.

19. The method of claim 12, further comprising:
   removing the sleeve after cutting the spacer.

20. The method of claim 12, further comprising:
   manipulating the spacer to adjust the position of the sling assembly before cutting the spacer.

21. The method of claim 12, wherein:
   a portion of the sleeve positioned away from the sling is affixed to the spacer at an end of the spacer that is farthest from the sling; and
   cutting the spacer comprises severing the end of the spacer from the spacer such that the sleeve is no longer affixed to the spacer.

22. A sling assembly comprising:
   a sleeve;
   an elongate sling, wherein the sleeve encloses at least a portion of the sling; and
   a structure coupled to at least a portion of the sleeve, the structure configured to space a portion of the sleeve away from the sling.

23. The system of claim 22, wherein the structure is a handle for positioning the sling assembly.

24. The system of claim 22, wherein the structure is affixed to a portion of the sleeve positioned away from the sling.

25. The system of claim 22, wherein the structure is a separate component from the sleeve.

* * * * *